(12) United States Patent
Angelidaki et al.

(10) Patent No.: US 11,193,142 B2
(45) Date of Patent: Dec. 7, 2021

(54) METHODS AND APPARATUS FOR HYDROGEN BASED BIOGAS UPGRADING

(71) Applicants: TECHNICAL UNIVERSITY OF DENMARK, Lyngby (DK); VESTFORSYNING A/S, Holstebro (DK)

(72) Inventors: Irini Angelidaki, Frederiksberg (DK); Poul Lyhne, Holstebro (DK); Gang Luo, Lyngby (DK)

(73) Assignee: AgorFora ApS, Korsor (DK)

( * ) Notice: Subject to any disclaimer, the term of this patent is extended or adjusted under 35 U.S.C. 154(b) by 1122 days.

(21) Appl. No.: 14/353,299

(22) PCT Filed: Oct. 12, 2012

(86) PCT No.: PCT/DK2012/050390
§ 371 (c)(1),
(2) Date: Aug. 4, 2014

(87) PCT Pub. No.: WO2013/060331
PCT Pub. Date: May 2, 2013

(65) Prior Publication Data
US 2014/0342426 A1 Nov. 20, 2014

Related U.S. Application Data

(60) Provisional application No. 61/563,247, filed on Nov. 23, 2011, provisional application No. 61/550,492, filed on Oct. 24, 2011.

(30) Foreign Application Priority Data

Oct. 24, 2011 (EP) ..................... 11186323

(51) Int. Cl.
*C12P 5/02* (2006.01)
*C12M 1/00* (2006.01)
*C12M 1/107* (2006.01)

(52) U.S. Cl.
CPC ............. *C12P 5/023* (2013.01); *C12M 21/04* (2013.01); *C12M 29/16* (2013.01); *C12M 43/00* (2013.01); *C12M 43/08* (2013.01); *C12M 47/18* (2013.01); *Y02E 50/30* (2013.01)

(58) Field of Classification Search
CPC ........ C12P 5/023; C12M 21/04; C12M 29/16; C12M 43/00; C12M 43/08; C12M 47/18; Y02E 50/30
USPC ....................................................... 435/167
See application file for complete search history.

(56) References Cited

U.S. PATENT DOCUMENTS

| 4,798,801 A * | 1/1989 | Hitzman | ................... B09B 1/00 435/290.1 |
|---|---|---|---|
| 4,897,359 A | 1/1990 | Oakley et al. | |
| 8,323,938 B2 | 12/2012 | Salvetzki | |
| 2006/0060526 A1 | 3/2006 | Binning et al. | |
| 2009/0130734 A1 | 5/2009 | Mets | |

FOREIGN PATENT DOCUMENTS

| DE | 10 2009 053 593 | | 5/2011 | |
|---|---|---|---|---|
| DE | 10 2010 043 630 | | 5/2011 | |
| DE | 102009053593 | * | 5/2011 | ............ C12M 1/107 |
| EP | 0 419 234 | | 3/1991 | |
| FR | 2537992 | | 6/1984 | |
| FR | 2537992 A1 | * | 6/1984 | ................ C12P 5/02 |
| GB | 2476090 | | 6/2011 | |
| JP | 2010162463 | * | 7/2010 | ............ B01D 53/22 |
| WO | WO2008/094282 | * | 7/2008 | ................ C12P 5/00 |
| WO | WO 2011/000084 | | 1/2011 | |

OTHER PUBLICATIONS

Magana-Ramirez et al. (Anaerobic treatment of lactic waste and goat manure. Ing. Investig. Apr. 2011 vol. 31(1) pp. 93-98).*
Fuentes-Arderiu et al. (Concentration and content. Biochemia Media 2013; 232):141-142).*
Comino et al. (Development of a pilot sale anaerobic digester for biogas production from cow manure and whey mix. Biosource Technology 100 (2009) 5072-5078).*
Pumphrey et al. (An Introduction to Fermentation: Fermentation Basics. New Brunswick Scientific Benelux BC. May 1996. pp. 1-26).*
Angelidaki et al. 2004 "Assesment of the anaerobic biodegradability of macropollutants" Rev Environ Sci Biotech 3: 117-129.
Celmer et al. 2008 "Impact of shear force on the biofilm structure and performance of a membrane biofilm reactor for tertiary hydrogen-driven denitrification of municipal wastewater" Water Research 42(12),3057-3065.
Luo et al. 2011 "Long-term effect of inoculum pretreatment on fermentative hydrogen production by repeated batch cultivations: homoacetogenesis and methanogenesis as competitors to hydrogen production" Biotech Bioeng 108: 1816-1827.
Siriwongrungson et al. 2007 "Homoacetogenesis as the alternative pathway for H2 sink during thermophilic anaerobic degradation of butyrate under suppressed methanogenesis" Water Res 41: 4204-4210.

* cited by examiner

*Primary Examiner* — Sharmila G Landau
*Assistant Examiner* — Natalie M Moss
(74) *Attorney, Agent, or Firm* — Hoffberg & Associates; Steven M. Hoffberg

(57) ABSTRACT

The present invention relates to an anaerobic process for biogas upgrading and hydrogen utilization comprising the use of acidic waste as co-substrate. In this process, $H_2$ and $CO_2$ will be converted to $CH_4$, which will result in lower $CO_2$ content in the biogas. The invention relates to both in situ and ex situ methods of biogas upgrading. The invention further relates to a bioreactor comprising hollow fibre membranes.

20 Claims, 10 Drawing Sheets

METHODS AND APPARATUS FOR HYDROGEN BASED BIOGAS UPGRADING

FIELD OF INVENTION

The present invention relates to the field of biogas upgrading in anaerobic biogas reactors by hydrogen utilization.

BACKGROUND OF INVENTION

The production and utilization of biogas by anaerobic digestion of organic wastes is an emerging alternative energy technology. Biogas is envisioned as a key element in emerging renewable energy strategies in Europe, motivated by the European Union target of achieving 20% renewable energy by 2020. The Danish government also proposed a target of using 50% of the manure produced in Denmark for renewable energy production by 2020, and it would essentially be met through a strong biogas expansion. Biogas mainly contains $CH_4$ (50-75%) and $CO_2$ (25-50%). Upgrading of biogas to $CH_4$ content higher than 90% can not only increase the heating value, but also reduce corrosion caused by acid gas and therefore extend the biogas utilization as a renewable energy source.

The common methods of biogas upgrading include water washing, pressure swing adsorption, polyglycol adsorption and chemical treatment, which aim to remove $CO_2$ from the biogas. The costs of the above methods are relatively high since they need either high pressure or addition of chemicals. Besides, when removing $CO_2$ from biogas, small amounts of $CH_4$ are also removed, which will possibly increase the greenhouse gas emission. To circumvent these disadvantages and use milder treatments with minimal chemical and energy, anaerobic microorganisms can be used to convert $CO_2$ to $CH_4$ for biogas upgrading (equation 1). The microorganisms are hydrogenotrophic methanogens within the orders Methanobacteriales, Methanococcales, Methanomicrobials et al. Anaerobic sludges in anaerobic reactors treating organic wastes contain the above microorganisms and have certain hydrogenotrophic-methanogenic potential. Therefore, hydrogen can be injected into an anaerobic reactor for in-situ $CO_2$ reduction and biogas upgrading.

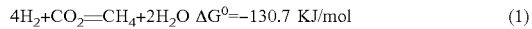

$$4H_2 + CO_2 = CH_4 + 2H_2O \quad \Delta G^0 = -130.7 \text{ KJ/mol} \qquad (1)$$

The $H_2$ used for $CH_4$ production from $CO_2$ can be obtained from wind mills. Commercial wind power has been produced in Denmark since 1970s, and wind power currently accounts for nearly 20% of the Danish electricity supply. Due to varying wind conditions and electricity demand over the year, up to 40% of the electricity from wind is judged to be surplus. An attractive way of exploiting wind mills capacity is to electrolyze water for $H_2$ production. In addition, $H_2$ can be also obtained by other sources, including coal gasification, petroleum refinery, petrochemical plants, and soda manufacture. Currently, hydrogen utilization has several yet unsolved bottlenecks such as hydrogen transport, storage, as well as utilization in the fuel cells. Therefore, conversion of hydrogen in a biogas plant would provide several advantages, such as utilization of the existing infrastructure of biogas plants. Additionally, conversion of hydrogen in a biogas reactor would consume some $CO_2$ in the biogas and thereby result in upgraded biogas with lower $CO_2$ content. This partial removal of $CO_2$ from the biogas would decrease the costs for the upgrading of biogas to natural gas quality, which could provide additional utilization opportunities of biogas, e.g. as vehicle fuel, as well as improving energy density and transmission capacity of the $CH_4$ enriched biogas. Finally, possible unconverted hydrogen mixed with methane, would improve the combustion properties of biogas as fuel (5-30% hydrogen by volume). The storage cost for methane is at least a 3 times lower compared to hydrogen, due to the higher boiling point and higher volumetric energy density of gaseous methane. Additionally, a number of countries already have natural gas infrastructure, which would make distribution of upgraded biogas feasible.

US 2009/013734 discloses a method for converting effluent $CO_2$ (g) from ethanol plants and $H_2$ (g) to $CH_4$ (g). The $H_2$ (g) is typically produced by hydrolysis using inexpensive off-peak electricity from power plants. The process is performed by microbial fermentation using methanogenic archaea.

SUMMARY OF INVENTION

Biogas is currently one of the fastest growing sources of energy. However, biogas is produced from biomass and contains a high proportion of $CO_2$ which has a low value as energy source. Thus it is desirable to decrease the content of $CO_2$ in biogas. This process, which often is referred to as upgrading of biogas, is facilitated by methanogenic organisms, preferably hydrogenotrophic methanogenic archaea. These organisms are preferably cultured at a pH of between 7-8. The process includes adding $H_2$ containing gas or pure $H_2$ (g) to a biogas reactor for in-situ biogas upgrading. The hydrogenotrophic methanogenic archaea utilises the $H_2$ to convert $CO_2$ of the biogas and/or $CO_2$ dissolved in the culture medium to $CH_4$.

However, as the process progresses, the $CO_2$ of the culture medium is consumed resulting in an increased pH of the culture medium. When pH exceeds 8.3 the process is inhibited as the culturing conditions for the methanogenic archaea has become sub-optimal. In order to solve this problem, the present inventors have demonstrated that the anaerobic digestion of the biomass, such as manure can be made in the presence of an acidic composition such as acidic waste from industry and/or agriculture, resulting in a sustained and high-performing process for upgrading biogas. The upgraded biogas can be utilised in existing gas grid infrastructure.

According to the present invention, the biogas upgrading may be performed in a single bioreactor, i.e. in situ, or in separate bioreactors, i.e. ex situ.

In one aspect the present invention relates to a method of manufacturing upgraded biogas in situ, said method comprising the steps of:
a. initiating an anaerobic digestion process in a bioreactor comprising:
   i. substrate,
   ii. anaerobic inoculum comprising anaerobic hydrogenotrophic methanogenic organisms
b. feeding the bioreactor with acidic waste having a pH<5,
c. feeding the bioreactor with biomass,
d. injecting $H_2$ containing gas into the bioreactor, and
e. collecting the upgraded biogas thus produced, wherein said upgraded biogas has a $CH_4$ content of at least 90%.

In one aspect the present invention relates to a method of manufacturing an upgraded biogas, wherein said biogas is further upgraded in a second bioreactor (ex situ) according to a method comprising the steps of:

a. initiating an anaerobic digestion process in a first bioreactor comprising:
   i. substrate,
   ii. anaerobic inoculum comprising anaerobic hydrogenotrophic methanogenic organisms,
b. feeding the first bioreactor with acidic waste having a pH<5.
c. feeding the bioreactor with biomass,
d. injecting $H_2$ containing gas into the first bioreactor,
e. transferring the biogas produced in the first bioreactor to a second bioreactor, wherein an anaerobic digestion process has been initiated with:
   i. nutrients,
   ii. anaerobic inoculum comprising anaerobic hydrogenotrophic methanogenic organisms,
f. feeding the second bioreactor with nutrients,
g. injecting $H_2$ containing gas into the second bioreactor, and
h. collecting the upgraded biogas thus produced, wherein said upgraded biogas has a $CH_4$ content of at least 95%.

In another aspect the present invention relates to a bioreactor comprising:
a. reactor vessel,
b. a gas injection system comprising hollow fibres
c. loading means for supply of substrates and or inoculum, and
d. discharge means for products and/or waste.

DETAILED DESCRIPTION OF THE INVENTION

Hydrogen Production and Utilisation

Figure 1:
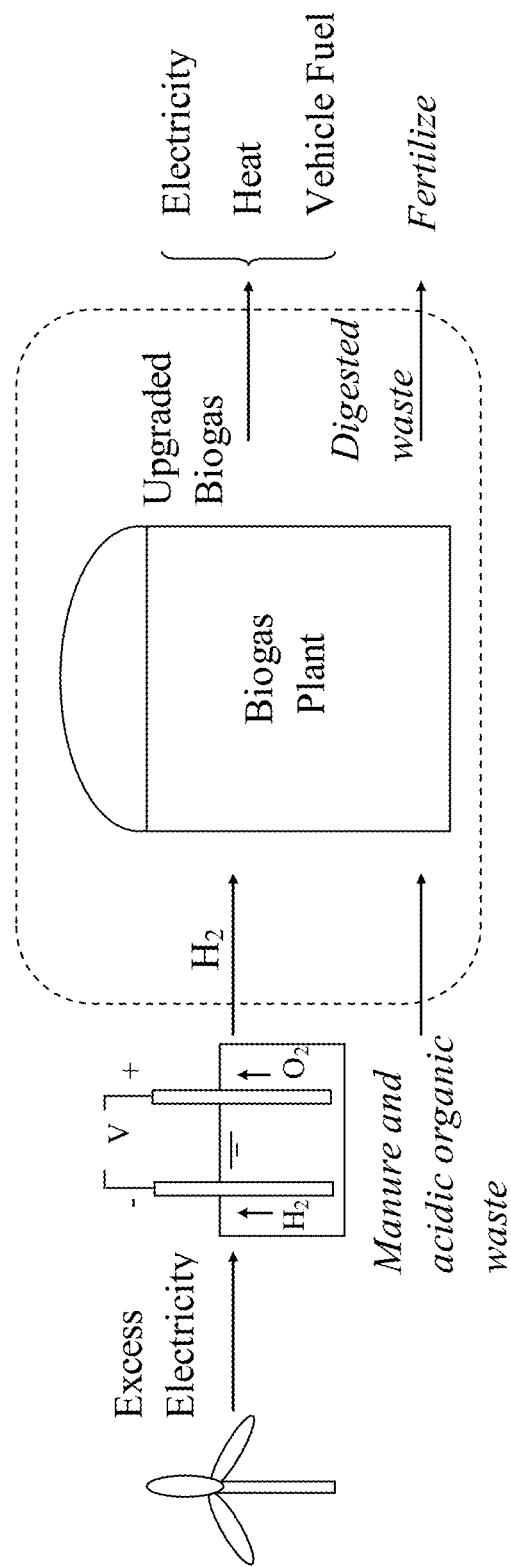
FIG. 1: Schematic overview of the plant and process of the invention.
Figure 2:
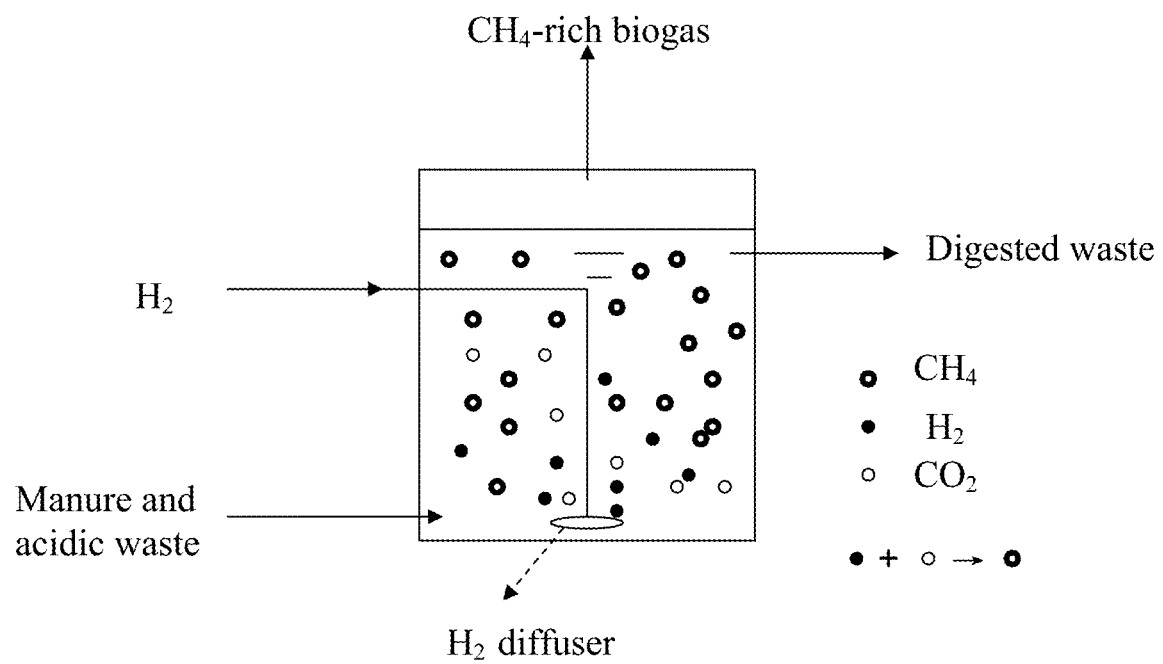
FIG. 2: One embodiment of the plant/method of the present invention.

Hydrogen ($H_2$) can be produced by electrolysis of water. To be economically favourable, this requires cheap electric power. The production of electric power in wind power plants varies over time due to wind conditions. The consumption of electric power also varies over time due to circadian rhythm and industrial needs. Hence occasionally the production of energy exceeds the consumption which thus produces surplus energy. The surplus energy can be utilised during off-peak hours to produce cheap $H_2$ by electrolysis of water.

Attempts to utilize $H_2$ as energy source in itself are environmentally very promising but at present techniques are not sufficiently efficient and economically favourable. One disadvantage is that hydrogen must be compressed and stored which is expensive.

Biogas

Another sustainable source of energy is biogas which typically is produced during digestion of biomass.

Biogas typically refers to a gas produced by the biological breakdown of organic matter in the absence of oxygen. Organic waste such as manure, dead plant and animal material, animal dung, and kitchen waste can be converted into a gaseous fuel called biogas. Biogas originates from biogenic material and is a type of biofuel.

Biogas is produced by the anaerobic digestion of biodegradable materials (biomass) such as manure, sewage, municipal waste, green waste, plant material, and crops. Biogas comprises primarily methane ($CH_4$) and carbon dioxide ($CO_2$) and may have small amounts of hydrogen sulphide (H2S), moisture and siloxanes.

The gases methane, hydrogen, and carbon monoxide (CO) can be combusted. Energy release through said combustion allows biogas to be used as a fuel. Biogas can be used as a fuel in any country for any heating purpose, such as cooking. It can also be used in anaerobic digesters where it is typically used in a gas engine to convert the energy in the gas into electricity and heat. Biogas can be compressed, much like natural gas, and used to power motor vehicles. In the UK, for example, biogas is estimated to have the potential to replace around 17% of vehicle fuel. Biogas is a renewable fuel, so it qualifies for renewable energy subsidies in some parts of the world. Biogas can also be cleaned and upgraded to natural gas standards when it becomes biomethane.

The composition of biogas varies depending upon the biomass and origin used for the anaerobic digestion process. However the composition of raw biogas produced by traditional methods typically ranges within the values summarized in table 1 below:

TABLE 1

| Compound | Formula | % |
| --- | --- | --- |
| Methane | $CH_4$ | 50-75 |
| Carbon dioxide | $CO_2$ | 25-50 |
| Nitrogen | $N_2$ | 0-10 |
| Hydrogen | $H_2$ | 0-1 |
| Hydrogen sulfide | $H_2S$ | 0-3 |
| Oxygen | $O_2$ | 0-0 |

The composition of biogas varies depending upon the origin of the anaerobic digestion process. Landfill gas typically has methane concentrations around 50%. Advanced waste treatment technologies can produce biogas with 55-75% $CH_4$, which for reactors with free liquids can be increased to 80-90% methane using in-situ gas purification techniques.

When biogas is used, many advantages arise. In North America, utilization of biogas would generate enough electricity to meet up to three percent of the continent's electricity expenditure. In addition, biogas could potentially help reduce global climate change. Normally, manure that is left to decompose releases two main gases that cause global climate change: nitrous dioxide and methane. Nitrous dioxide ($N_2O$) warms the atmosphere 310 times more than carbon dioxide and methane 21 times more than carbon dioxide. By converting cow manure into methane biogas via anaerobic digestion, the millions of cows in the United States would be able to produce one hundred billion kilowatt hours of electricity, enough to power millions of homes across the United States. In fact, one cow can produce enough manure in one day to generate three kilowatt hours of electricity; only 2.4 kilowatt hours of electricity are needed to power a single one hundred watt light bulb for one day. Furthermore, by converting cow manure into methane biogas instead of letting it decompose, it would be possible to reduce global warming gases by ninety-nine million metric tons or four percent.

The 30 million rural households in China that have biogas digesters enjoy 12 benefits: saving fossil fuels, saving time collecting firewood, protecting forests, using crop residues for animal fodder instead of fuel, saving money, saving cooking time, improving hygienic conditions, producing high-quality fertilizer, enabling local mechanization and electricity production, improving the rural standard of living, and reducing air and water pollution.

In Situ Biogas Upgrading

As mentioned herein above raw biogas produced from digestion in traditional biogas reactors is roughly 60% methane and 40% $CO_2$. The high $CO_2$ content makes the biogas less attractive for direct use as energy source. The solution is the use of a biogas upgrading or purification process whereby contaminants in the raw biogas stream are absorbed or scrubbed, leaving up to 98% methane per unit volume of gas. Traditionally there have been four main methods of biogas upgrading including water washing, pressure swing absorption, selexol absorption, and amine gas treating. The most prevalent method is water washing where high pressure gas flows into a column where the carbon dioxide and other trace elements are scrubbed by cascading water running counter-flow to the gas. Present day arrangement, however, are expensive and impractical as they require a further step before the biogas can be utilised. The present inventors have demonstrated that it is possible to obtain large quantities of high-grade (high content $CH_4$) biogas by in situ utilisation of $H_2$ containing gas or pure $H_2$ (g).

The inventors have demonstrated that $H_2$, such as $H_2$ produced by electrolysis of water using off-peak hours excess electric power, can be utilised directly in a biogas reactor, thus avoiding expensive compression and storage, for upgrading biogas by converting $CO_2$ in the biogas to methane ($CH_4$). The upgraded biogas can be utilised in an existing natural gas grid infrastructure and/or to directly as a fuel source.

The process can make use of existing infrastructure of biogas plants and it is therefore a cheap method for upgrading of biogas.

Conversion of $CO_2$ to $CH_4$ using $H_2$ has the following problem—when hydrogen is injected into a bioreactor comprising methanogens, and reacts with $CO_2$ to produce $CH_4$, the pH increases due to bicarbonate consumption. When the pH exceeds 8.3, the biological conversion process will be inhibited, because methanogens cannot grow well at this high pH. In order to achieve in situ biogas upgrading and hydrogen utilization with high efficiency, the present inventors have demonstrated that biogas can be produced by co-digestion of manure with acidic wastes. Several acidic wastes can be used as substrates for co-digestion with biomass, such as manure. Examples of acidic wastes include but are not limited to whey wastes, stillage (wastewater from ethanol production) and fruit juice from potato processing industries. The acidic waste thus contributes to keeping the pH in an optimal range of between 7 and 8. Hence the anaerobic process is allowed to proceed without inhibition. A further benefit of the acidic waste is that it can also functions as a substrate for microbial conversion.

The acidic waste usually has a pH lower than about 5.5, such as a pH of about or lower than 5.0, for example a pH of about or lower than 4.5. For example, the pH of whey is about 4 to 5, such as about 4.5.

The acidic waste is in one embodiment mixed with the biomass, such as manure, to create a mixture before being fed to the reactor. This results in a lowering of the pH of the composition which is fed to the reactor. The ratio of acidic waste to biomass is usually about 2:3. However, in other embodiments, the ratio may be about 1:1. The ratio depends on the pH of the acidic waste added. The pH of the mixture of biomass and acidic waste is preferably less than 7.

In another embodiment, the acidic waste is fed to the reactor separately from the biomass.

The acidic waste, which may be added together with the biomass or separately from the biomass, may be fed to the reactor once, twice, or several times a day. The essential criterion is that the pH of the reactor is kept in the optimal range of pH 7 to 8 for the anaerobic process to proceed without inhibition. The acidic waste thus acts to stabilize the pH at an optimal level as $CO_2$ is removed from the biogas which in the absence of acidic compositions such as acidic waste would render the pH to increase.

Accordingly, in one aspect the present invention relates to a method of manufacturing an upgraded biogas, said method comprising the steps of:
a. initiating an anaerobic digestion process in a bioreactor comprising:
  i. substrate,
  ii. anaerobic inoculum comprising anaerobic hydrogenotrophic methanogenic organisms
b. feeding the bioreactor with acidic waste having a pH<5,
c. feeding the bioreactor with biomass,
d. injecting $H_2$ containing gas into the bioreactor, and
e. collecting the upgraded biogas thus produced, wherein said upgraded biogas has a $CH_4$ content of at least 90%.

The substrate is usually biomass comprising the nutrients necessary for the initiation of the anaerobic digestion process; however, the substrate may also consist of nutrients only. The term "nutrients" is to be understood as micro and macro nutrients necessary for microbial growth.

The expression "biomass" as used herein is to be understood as products consisting of organic or vegetable matter from agriculture or forestry, which material can be used as fuel for the extraction of the energy content of the material. Typically, the biomass is protein-rich organic waste, including but not limited to manure, activated sludge from wastewater treatment plant, fish processing residues, etc.

A prerequisite for producing biogas is to have a substrate such as biomass that can be converted to biogas. Biomass is typically used in the initiation of the anaerobic process but is also fed to the bioreactor repeatedly during the biogas production process, such as once, twice, or three times a day. Alternatively, the anaerobic process may be initiated with a minimal nutrients solution only and the biomass is added at a later stage, for example at the same time as the acidic waste.

It is furthermore understood that anaerobic inoculum normally comprises anaerobic hydrogenotrophic methanogenic organisms such as anaearobic hydrogenotrophoc archaea. The inoculum may also contain one or more types of microorganisms selected from the group consisting of hydrolytic, acidogenic, acetogenic and methanogenic microorganisms.

Anaerobic inoculum is sometimes also referred to as anaerobic sludge.

The expression high $CH_4$ content biogas is to be understood as a biogas having a $CH_4$ content exceeding that of conventional non-upgraded biogas. Hence, according to the present invention, a "high $CH_4$ content biogas" typically contains at least 90% $CH_4$, such as at least 91% $CH_4$, for example at least 92% $CH_4$, such as at least 93% $CH_4$, for example at least 94% $CH_4$, such as at least 95% $CH_4$, for example at least 96% $CH_4$, such as at least 97% $CH_4$, for example at least 98% $CH_4$, such as at least 99% $CH_4$, for example at least 99.5% $CH_4$, such as at least 99.6% $CH_4$, for example at least 99.7% $CH_4$, such as at least 99.8% $CH_4$, for example at least 99.9% $CH_4$ as measured by $CH_4$ content of the biogas.

In one embodiment of the method of the present invention the pH in the bioreactor is maintained below 8.3.

In another embodiment of the method of the present invention the pH in the bioreactor is maintained below 8.0.

In one embodiment the pH is maintained between 7 and 8. As mentioned, this can be achieved by the process of co-digesting biomass with acidic waste.

In one embodiment the ratio of biomass to acidic waste is experimentally determined to maintain the pH between 7 and 8.

In one embodiment the ratio of biomass to acidic waste fed to the bioreactor is 3 to 2.

In one embodiment the ratio of biomass to acidic waste fed to the bioreactor is 1 to 1.

In one embodiment the method of the present invention further comprises the step of separating $CH_4$ (g) from the other components of the high $CH_4$ content biogas produced, thus producing a substantially pure $CH_4$ (g).

In one embodiment, the biogas produced by the present invention is further upgraded by traditional methods of upgrading biogas.

In one embodiment, the biogas produced by the present invention is added propane to adjust the burn value of the gas.

In one embodiment the $H_2$ containing gas is added continuously to the bioreactor.

In one embodiment a gas injection system comprising hollow fibres is used to introduce the $H_2$ into the bioreactor.

The method of manufacturing an upgraded biogas comprises the process of increasing the $CH_4$ content of the biogas, thus in one aspect the present invention relates to a method for increasing $CH_4$ content in biogas in situ, said method comprising the steps of:
  a. initiating an anaerobic digestion process in a bioreactor comprising:
    i. substrate,
    ii. anaerobic inoculum comprising anaerobic hydrogenotrophic methanogenic organisms
  b. feeding the bioreactor with acidic waste having a pH<5,
  c. feeding the bioreactor with biomass,
  d. injecting $H_2$ containing gas into the bioreactor, and
  e. collecting the upgraded biogas thus produced, wherein said upgraded biogas has a $CH_4$ content of at least 90%.

Likewise, the method of manufacturing an upgraded biogas comprises the process of decreasing the $CO_2$ content of the biogas, hence in one aspect the present invention relates to a method for reducing $CO_2$ (g) content in biogas, said method comprising the steps of:
  a. initiating an anaerobic digestion process in a bioreactor comprising:
    i. substrate,
    ii. anaerobic inoculum comprising anaerobic hydrogenotrophic methanogenic organisms
  b. feeding the bioreactor with acidic waste having a pH<5,
  c. feeding the bioreactor with biomass,
  d. injecting $H_2$ containing gas into the bioreactor, and
  e. collecting the upgraded biogas thus produced, wherein said upgraded biogas has a $CH_4$ content of at least 90%.

By removing the low energy content $CO_2$ from the biogas, the overall energy content of the biogas is increased. Hence in one aspect the present invention relates to a method for increasing energy content of biogas, said method comprising the steps of:
  a. initiating an anaerobic digestion process in a bioreactor comprising:
    i. substrate,
    ii. anaerobic inoculum comprising anaerobic hydrogenotrophic methanogenic organisms,
  b. feeding the bioreactor with acidic waste having a pH<5,
  c. feeding the bioreactor with biomass,
  d. injecting $H_2$ containing gas into the bioreactor, and
  e. collecting the upgraded biogas thus produced, wherein said upgraded biogas has a $CH_4$ content of at least 90%.

By utilising the process of the invention comprising the element of co-digesting biomass such as manure with acidic compositions such as acidic waste products, the process is sustained as no inhibition of the process occurs due to increased pH in the bioreactor. Hence, in another aspect the present invention relates to a method for sustained anaerobic conversion of $CO_2$ to $CH_4$, said method comprising:
  a. initiating an anaerobic digestion process in a bioreactor comprising:
    i. substrate,
    ii. anaerobic inoculum comprising anaerobic hydrogenotrophic methanogenic organisms,
  b. feeding the bioreactor with acidic waste having a pH<5,
  c. feeding the bioreactor with biomass,
  d. injecting $H_2$ containing gas into the bioreactor, and
  e. collecting the upgraded biogas thus produced, wherein said upgraded biogas has a $CH_4$ content of at least 90%.

By lowering the amount of $CO_2$ of the biogas contained in e.g. a biogas reactor the partial pressures of the biogas components are altered. Accordingly, in one aspect the present invention relates to a method for increasing the partial pressure of $CH_4$ in biogas, said method comprising:
  a. initiating an anaerobic digestion process in a bioreactor comprising:
    i. substrate,
    ii. anaerobic inoculum comprising anaerobic hydrogenotrophic methanogenic organisms,
  b. feeding the bioreactor with acidic waste having a pH<5,
  c. feeding the bioreactor with biomass,
  d. injecting $H_2$ containing gas into the bioreactor, and
  e. collecting the upgraded biogas thus produced, wherein said upgraded biogas has a $CH_4$ content of at least 90%.

Likewise by increasing the amount of $CH_4$ of the biogas contained in e.g. a biogas reactor the partial pressure of the biogas components are altered. Accordingly in one aspect the present invention relates to a method for decreasing the partial pressure of $CO_2$ in biogas, said method comprising:

a. initiating an anaerobic digestion process in a bioreactor comprising:
   i. substrate,
   ii. anaerobic inoculum comprising anaerobic hydrogenotrophic methanogenic organisms,
b. feeding the bioreactor with acidic waste having a pH<5,
c. feeding the bioreactor with biomass,
d. injecting $H_2$ containing gas into the bioreactor, and
e. collecting the upgraded biogas thus produced, wherein said upgraded biogas has a $CH_4$ content of at least 90%.

The upgraded biogas so produced may, if the $CH_4$ content is sufficiently high, be used directly in the natural gas grid infrastructure.

In one aspect, the biogas is further upgraded with the aim of obtaining a gas suitable for use in the natural gas grid infrastructure or the biogas is purified further to obtain substantially pure methane.

In one aspect the present invention relates to the use of the upgraded biogas as vehicle fuel.

In another aspect the present invention relates to the use of the upgraded biogas in a heating power plant such as a district heating power plant.

In another aspect the present invention relates to the use of the upgraded biogas for electricity production.

Ex Situ Biogas Upgrading

To achieve an even higher concentration of $CH_4$ in the biogas, it may be advantageous to upgrade the biogas produced by the in situ methods described above even further in a separate reactor, i.e. by utilising an ex situ method.

Hence, it may be advantageous to apply the present methods for upgrading biogas manufactured externally and transported to the bioreactor of the present invention. In one aspect the present invention thus concerns a method of manufacturing an upgraded high $CH_4$ content biogas, said method comprising the steps of:
a. initiating an anaerobic digestion process in a bioreactor comprising:
   i. substrate,
   ii. anaerobic inoculum comprising anaerobic hydrogenotrophic methanogenic organisms,
b. feeding the bioreactor with acidic waste having a pH<5,
c. feeding the bioreactor with biomass,
d. injecting $H_2$ containing gas and biogas into the bioreactor, and
e. collecting the upgraded biogas thus produced, wherein said upgraded biogas has a $CH_4$ content of at least 90%.

In one aspect the present invention relates to a method of manufacturing an upgraded high $CH_4$ content biogas, wherein said biogas is produced in a first reactor according to the in situ methods of the present invention, followed by a further upgrading of the $CH_4$ content of the biogas in a second bioreactor (ex situ) according to a method comprising the steps of:
a. initiating an anaerobic digestion process in a first bioreactor comprising:
   i. substrate,
   ii. anaerobic inoculum comprising anaerobic hydrogenotrophic methanogenic organisms,
b. feeding the first bioreactor with acidic waste having a pH<5,
c. feeding the bioreactor with biomass,
d. injecting $H_2$ containing gas into the first bioreactor,
e. transferring the biogas produced in the first bioreactor to a second bioreactor, wherein an anaerobic digestion process has been initiated with:
   i. nutrients,
   ii. anaerobic inoculum comprising anaerobic hydrogenotrophic methanogenic organisms,
f. feeding the second bioreactor with nutrients,
h. collecting the upgraded biogas thus produced, wherein said upgraded biogas has a $CH_4$ content of at least 95%.

The nutrients may e.g. be a wastewater solution. The skilled person is able to provide a suitable nutrients solution for optimal microbial growth.

In one embodiment the $H_2$ containing gas is co-injected into the bioreactor together with the biogas.

In another embodiment the $H_2$ containing gas is injected into the bioreactor prior to the injection of the biogas.

In yet another embodiment the $H_2$ containing gas is injected into the bioreactor subsequently to the injection of the biogas.

The anaerobic inoculum typically contains anaerobic organisms such as anaerobic archaea. Thus in one embodiment the anaerobic hydrogenotrophic methanogenic organism is contained in anaerobic sludge. In another embodiment the anaerobic hydrogenotrophic methanogenic organism is contained in anaerobic inoculum.

The anaerobic organisms do not need to be supplied with biomass for growth in the second bioreactor. They are capable of growing solely on the supplied nutrients solution and by converting the $H_2$ and $CO_2$ into $CH_4$. The result is an upgraded biogas with a very high $CH_4$ content.

With the ex situ method it is possible to obtain an upgraded biogas having at least 95% $CH_4$, for example at least 96% $CH_4$, such as at least 97% $CH_4$, for example at least 98% $CH_4$, such as at least 99% $CH_4$, for example at least 99.5% $CH_4$, such as at least 99.6% $CH_4$, for example at least 99.7% $CH_4$, such as at least 99.8% $CH_4$, for example at least 99.9% $CH_4$ as measured by $CH_4$ content of the biogas.

In one embodiment, the $CH_4$ content of the upgraded biogas produced by the methods of the present invention is at least 97.3%.

In one embodiment a gas injection system comprising hollow fibres is used to introduce the $H_2$ and biogas into the second bioreactor.

Hydrogen Gas

The methods of the present invention utilise $H_2$ containing gas as one of the substrates in the conversion of $CO_2$ to $CH_4$. The $H_2$ containing gas may be pure $H_2$ or $H_2$ in combination with other gases. Preferably the $H_2$ containing gas is pure $H_2$. Thus in one embodiment the $H_2$ containing gas mentioned herein above consists essentially of $H_2$ (g).

Hydrogen gas or hydrogen containing gas can be produced by any process known to those skilled in the art. Preferably the $H_2$ (g) is produced by utilising excess electric power from a sustainable energy power plant for the hydrolysis of water thus producing $H_2$ (g). In one embodiment the sustainable energy power plant is a wind power plant.

In another embodiment the $H_2$ containing gas is obtained from coke oven gas, syngas from biomass gasification and/or waste gas from chemical process industries such as hydrogen from production of potassium chlorate.

Biogas Utilisation

Biogas can be utilized for electricity production on sewage works in a CHP gas engine, where the waste heat from the engine is conveniently used for heating the digester; cooking; space heating; water heating; and process heating. If compressed, it can replace compressed natural gas for use in vehicles, where it can fuel an internal combustion engine or fuel cells and is a much more effective displacer of carbon dioxide than the normal use in on-site CHP plants.

Methane within biogas can be concentrated via a biogas upgrader to the same standards as fossil natural gas, which itself has had to go through a cleaning process, and becomes biomethane. If the local gas network allows for this, the producer of the biogas may utilize the local gas distribution networks. Gas must be very clean to reach pipeline quality, and must be of the correct composition for the local distribution network to accept. Carbon dioxide, water, hydrogen sulfide, and particulates must be removed if present.

The requirements to the purity and composition of the biogas for distribution in the natural gas grid infrastructure vary in different countries. For instance, the Danish national requirements to biogas include e.g. a wobbe index in the range of 50.8 to 55.8 MJ/Nm$^3$ and a $CO_2$ content less than 2.5%. For example, a biogas with a $CH_4$ content of 97.3% has an acceptable wobbe index and may be used directly in the Danish natural gas grid infrastructure.

In one embodiment, the biogas produced by the present invention is added propane to adjust the burn value (wobbe index) of the gas.

In one aspect the biogas upgraded by the process of the present invention is used as vehicle fuel.

In one embodiment the biogas upgraded by the process of the present invention is used in a heating power plant such as a district heating power plant.

In another embodiment the biogas upgraded by the process of the present invention is used for electricity production.

Fertilizer

As mentioned herein above, the method of the present invention can utilize manure such as cattle manure for co-digestion with acidic waste in the reactor. The digested manure is useful for several industrial and agricultural purposes such as a fertilizer.

Thus in one aspect the present invention relates to a method of manufacturing digested manure, said method comprising:
　a. initiating an anaerobic digestion process in a bioreactor comprising:
　　i. substrate,
　　ii. anaerobic inoculum comprising anaerobic hydrogenotrophic methanogenic organisms,
　b. feeding the bioreactor with acidic waste having a pH<5,
　c. feeding the bioreactor with biomass comprising undigested manure,
　d. injecting $H_2$ containing gas into the bioreactor, and
　e. collecting the digested manure.

In one embodiment the digested manure is used as a fertilizer. In another embodiment the method further comprises refining the digested manure to commercial grade fertilizer.

Bioreactor of the Invention

In one aspect the present invention concerns a bioreactor comprising:
　a. biomass,
　b. hydrogenotrophic methanogenic organisms,
　c. $H_2$ containing gas, and
　d. acidic waste.

Figure 3:
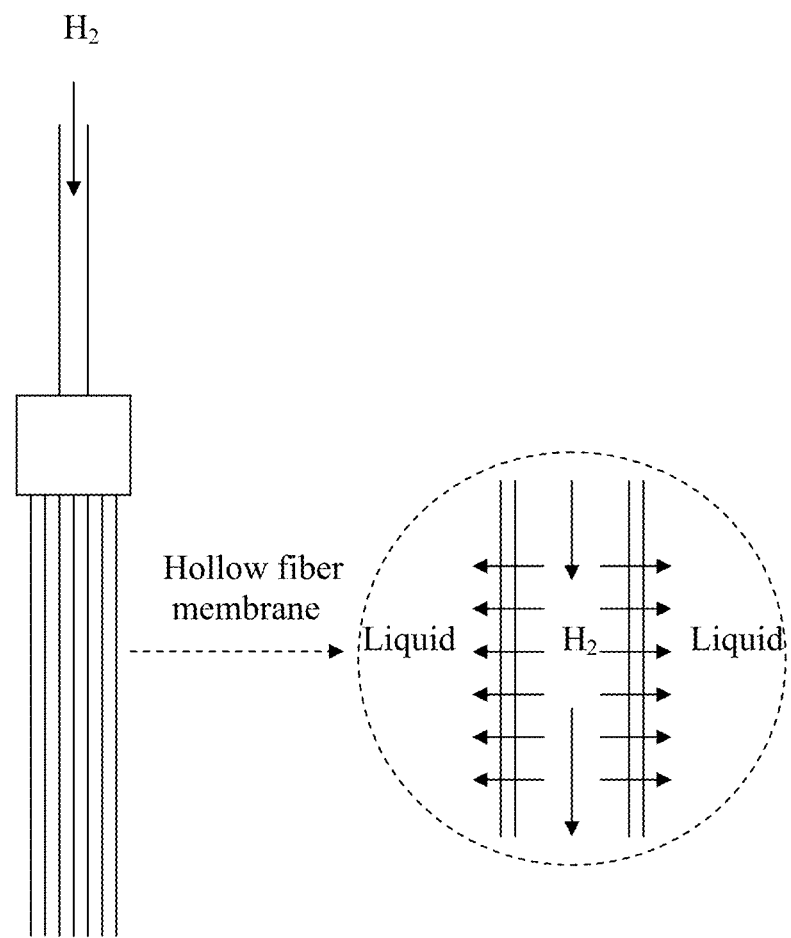
FIG. 3: Injection system comprising hollow fiber membrane for optimized gas diffusion.
Figure 4:
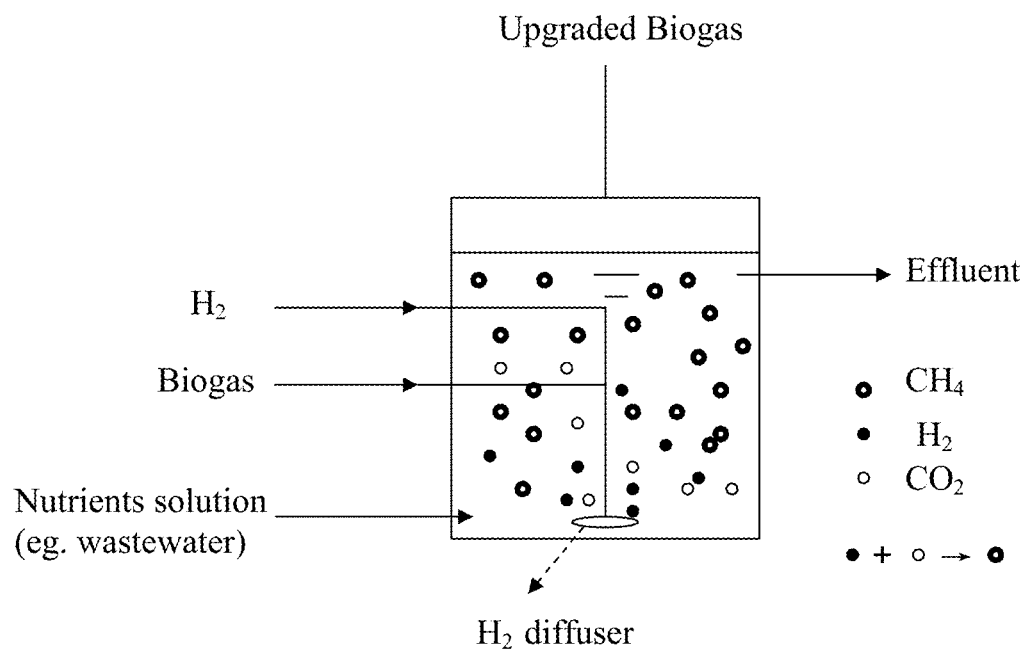
FIG. 4: Schematic ex-situ biogas upgrading reactor

The present inventors have demonstrated that the methods for upgrading biogas according to the present invention is particularly efficient if a bioreactor is used which comprises a particular gas injection system capable of injecting hydrogen containing gas into the fluid phase of the bioreactor content, without causing bubbles. Such an injection system with hollow fibre membranes is illustrated in FIG. 3.

$H_2$ is a gaseous substrate, and it is not easily captured by the microorganisms in the liquid phase. Full utilization of $H_2$ is important to further increase the $CH_4$ content in the biogas. Bubbleless gas-transfer via hollow fibre membrane (HFM) is a potential method to achieve the purpose of complete utilization of $H_2$. Gas inside the HFM can be delivered into the liquid phase through membranes by diffusion. Thus, the gas is directly dissolved in the liquid, no bubble is formed and the $H_2$ is taken up by the microorganisms more efficiently.

Hence, in one aspect, the present invention relates to a bioreactor comprising:
　a. a reactor vessel,
　b. a gas injection system comprising hollow fibre membranes,
　c. loading means for supply of substrates and or inoculum, and
　d. discharge means for products and/or waste.

The gas injection system comprising hollow fibre membranes is used to introduce $H_2$ containing gas into the bioreactor.

The gas injection system comprising hollow fibre membranes may also be used to introduce biogas into the bioreactor for ex situ biogas upgrading.

In one aspect the bioreactor comprises biomass, acidic waste and/or nutrients. The biomass, acidic waste and nutrients of the reactor are as defined herein above.

In one aspect the bioreactor comprises anaerobic inoculum comprising hydrogenotrophic methanogenic organisms.

In one aspect the bioreactor comprises $H_2$ containing gas.

In one aspect the bioreactor comprises acidic waste.

Hydrogenotrophic Methanogenic Organisms

The methods, uses and products of the present invention makes use of hydrogenotrophic methanogenic organisms.

In one embodiment, the hydrogenotrophic methanogenic organisms comprises one or more hydrogenotrophic methanogenic archaea, such as one or more species selected from the group consisting of *Methanobacterium alcaliphilum*, *Methanobacterium bryantii*, *Methanobacterium congolense*, *Methanobacterium defluvii*, *Methanobacterium espanolae*, *Methanobacterium formicicum*, *Methanobacterium ivanovii*, *Methanobacterium palustre*, *Methanobacterium thermaggregans*, *Methanobacterium uliginosum*, *Methanobrevibacter acididurans*, *Methanobrevibacter arboriphilicus*, *Methanobrevibacter gottschalkii*, *Methanobrevibacter olleyae*, *Methanobrevibacter ruminantium*, *Methanobrevibacter smithii*, *Methanobrevibacter woesei*, *Methanobrevibacter wolinii*, *Methanothermobacter marburgensis*, *Methanothermobacter thermautotrophicum*, *Methanothermobacter thermoflexus*, *Methanothermobacter thermophilus*, *Methanothermobacter wolfeii*, *Methanothermus sociabilis*, *Methanocorpusculum bavaricum*, *Methanocorpusculum parvum*, *Methanoculleus chikuoensis*, *Methanoculleus submarinus*, *Methanogenium frigidum*, *Methanogenium liminatans*, *Methanogenium marinum*, *Methanosarcina acetivorans*, *Methanosarcina barkeri*, *Methanosarcina mazei*, *Methanosarcina thermophila*, *Methanomicrobium mobile*, *Methanocaldococcus jannaschii*, *Methanococcus aeolicus*, *Methanococcus maripaludis*, *Methanococcus vannielii*, *Methanococcus voltaei*, *Methanothermococcus thermolithotrophicus*, *Methanopyrus kandleri*, *Methanothermobacter thermoautotroiphicus*, *Methanoca/dococcus fervens*, *Methanocaldococcus indicus*, *Methanocaldococcus infernus*, and *Methanocaldococcus vulcanius*.

In one embodiment the hydrogenotrophic methanogenic organism is a substantially pure culture of one hydrogenotrophic methanogenic archaea species.

In one embodiment the conditions of the bioreactor include a temperature of 35° C. to 37° C.

In one embodiment the hydrogenotrophic methanogenic archaea is Methanothermobacter thermoautotroiphicus.

In another embodiment the conditions of the bioreactor include a temperature of 50° C. to 60° C.

In one embodiment the hydrogenotrophic methanogenic archaea is selected from the group consisting of *Methanocaldococcus fervens*, *Methanocaldococcus indicus*, *Methanocaldococcus infernus*, and *Methanocaldococcus vulcanius*.

In yet another embodiment the conditions of the bioreactor include a temperature of 80° C. to 100° C.

Items

1. A method of manufacturing a high $CH_4$ content biogas, said method comprising the steps of:
   a. initiating an anaerobic digestion process in a bioreactor comprising a first composition comprising:
      i. substrate,
      ii. anaerobic inoculum
   b. feeding the bioreactor with a second composition having a pH below that of the first composition,
   c. injecting $H_2$ containing gas into the bioreactor,
   d. collecting the upgraded, high content $CH_4$ content biogas thus produced.

2. A method for increasing $CH_4$ content in biogas, said method comprising the steps of:
   a. initiating an anaerobic digestion process in a bioreactor comprising a first composition comprising:
      i. substrate,
      ii. anaerobic inoculum comprising anaerobic hydrogenotrophic methanogenic organisms
   b. feeding the bioreactor with a second composition having a pH below that of the first composition,
   c. injecting $H_2$ containing gas into the bioreactor,
   d. collecting the upgraded biogas thus produced.

3. A method for reducing $CO_2$ (g) content in biogas, said method comprising the steps of:
   a. initiating an anaerobic digestion process in a bioreactor comprising a first composition comprising:
      i. substrate,
      ii. anaerobic inoculum comprising anaerobic hydrogenotrophic methanogenic organisms
   b. feeding the bioreactor with a second composition having a pH below that of the first composition,
   c. injecting $H_2$ containing gas into the bioreactor,
   d. collecting the upgraded biogas thus produced.

4. A method for increasing energy content of biogas, said method comprising the steps of:
   a. initiating an anaerobic digestion process in a bioreactor comprising a first composition comprising:
      i. substrate,
      ii. anaerobic inoculum comprising anaerobic hydrogenotrophic methanogenic organisms
   b. feeding the bioreactor with a second composition having a pH below that of the first composition,
   c. injecting $H_2$ containing gas into the bioreactor,
   d. collecting the upgraded biogas thus produced.

5. A method for sustained anaerobic conversion of $CO_2$ to $CH_4$, said method comprising:
   a. initiating an anaerobic digestion process in a bioreactor comprising a first composition comprising:
      i. substrate,
      ii. anaerobic inoculum comprising anaerobic hydrogenotrophic methanogenic organisms
   b. feeding the bioreactor with a second composition having a pH below that of the first composition,
   c. injecting $H_2$ containing gas into the bioreactor,
   d. collecting the upgraded biogas thus produced.

6. A method for increasing the partial pressure of $CH_4$ in biogas, said method comprising:
   a. initiating an anaerobic digestion process in a bioreactor comprising a first composition comprising:
      i. substrate,
      ii. anaerobic inoculum comprising anaerobic hydrogenotrophic methanogenic organisms
   b. feeding the bioreactor with a second composition having a pH below that of the first composition,
   c. injecting $H_2$ containing gas into the bioreactor,
   d. collecting the upgraded biogas thus produced.

7. A method for decreasing the partial pressure of $CO_2$ in biogas, said method comprising:
   a. initiating an anaerobic digestion process in a bioreactor comprising a first composition comprising:
      i. substrate,
      ii. anaerobic inoculum comprising anaerobic hydrogenotrophic methanogenic organisms feeding the bioreactor with a second composition having a pH below that of the first composition,
   b. injecting $H_2$ containing gas into the bioreactor,
   c. collecting the upgraded biogas thus produced.

8. A method of manufacturing an upgraded high $CH_4$ content biogas, said method comprising the steps of:
   a. initiating an anaerobic digestion process in a bioreactor comprising:
      i. substrate,
      ii. anaerobic inoculum comprising anaerobic hydrogenotrophic methanogenic organisms,
   b. injecting $H_2$ containing gas and biogas into the bioreactor, and
   c. collecting the upgraded, high $CH_4$ content biogas thus produced.

9. The method of item 8 wherein the $H_2$ containing gas is co-injected into the bioreactor together with the biogas.

10. The method of item 8 wherein the $H_2$ containing gas is injected into the bioreactor prior to the injection of the biogas.

11. The method of item 8 wherein the $H_2$ containing gas is injected into the bioreactor subsequently to the injection of the biogas.

12. The method of any of items 1 to 11, wherein the substrate is biomass.

13. The method of any of the preceding items wherein the high $CH_4$ content biogas contains at least 50% $CH_4$, such as at least 60% $CH_4$, such as at least 70% $CH_4$, such as at least 75% $CH_4$, such as at least 76% $CH_4$, such as at least 77% $CH_4$, such as at least 78% $CH_4$, such as at least 79% $CH_4$, such as at least 80% $CH_4$, such as at least 81% $CH_4$, such as at least 82% $CH_4$, such as at least 83% $CH_4$, such as at least 84% $CH_4$, such as at least 85% $CH_4$, such as at least 86% $CH_4$, such as at least 87% $CH_4$, such as at least 88% $CH_4$, such as at least 89% $CH_4$, such as at least 90% $CH_4$, such as at least 91% $CH_4$, such as at least 92% $CH_4$, such as at least 93% $CH_4$, such as at least 94% $CH_4$, such as at least 95% $CH_4$, such as at least 96% $CH_4$, such as at least 97% $CH_4$, such as at least 98% $CH_4$, such as at least 99% $CH_4$, such as at least 99.5% $CH_4$, as measured by $CH_4$ content of the biogas.

14. The method of any of items 1 to 11, wherein the $H_2$ containing gas consists essentially of $H_2$ (g).

15. The method of any of the preceding items wherein the $H_2$ containing gas is produced by utilising excess electric power from a sustainable energy power plant for the hydrolysis of water thus producing $H_2$ (g).

16. The method of item 10, wherein the sustainable energy power plant is a wind power plant.
17. The method of any of items 1 to 14, wherein the $H_2$ containing gas is obtained from coke oven gas, syngas from biomass gasification and/or waste gas from chemical process industries such as hydrogen from production of potassium chlorate.
18. The method of any of items 1 to 7 wherein the second composition further comprises biomass.
19. The method of any of the preceding items wherein the biomass is protein-rich waste.
20. The method of any of the preceding items wherein the biomass is manure.
21. The method of any of the preceding items wherein the second composition comprises acidic waste.
22. The method of item 21 wherein the acidic waste is carbohydrate-rich waste selected from the group consisting of whey waste, stillage and fruit juice from potato processing industries.
23. The method of any of the preceding items wherein the pH in the bioreactor is maintained below 8.5.
24. The method of any of the preceding items wherein the pH in the bioreactor is maintained below 8.3.
25. The method of any of the preceding items wherein the pH in the bioreactor is maintained below 8.
26. The method of any of the preceding items wherein the pH is maintained between 7 and 8.
27. The method of item 26, wherein the pH is maintained between 7 and 8 by the process of co-digesting biomass with acidic waste.
28. The method of any of items 21 to 27 wherein the ratio of biomass to acidic waste is experimentally determined to maintain the pH between 7 and 8.
29. The method of any of items 21 to 28 wherein the ratio of biomass to acidic waste is 3 to 2.
30. The method of any of items 21 to 28 wherein the ratio of biomass to acidic waste is 1 to 1.
31. The method of any of the preceding items further comprising the step of separating $CH_4$ (g) from the other components of the upgraded biogas produced, thus producing a substantially pure $CH_4$ (g).
32. Use of the upgraded biogas of any of items 1 to 8, and/or the substantially pure $CH_4$ (g) of item 31 as vehicle fuel.
33. Use of the upgraded biogas of any of items 1 to 8, and/or the substantially pure $CH_4$ (g) of item 31 in a heating power plant such as a district heating power plant.
34. Use of the upgraded $CH_4$ content biogas of any of items 1 to 8, and/or the substantially pure $CH_4$ (g) of item 31 for electricity production.
35. A method of manufacturing digested manure, said method comprising:
    a. initiating an anaerobic digestion process in a bioreactor comprising a first composition comprising:
        i. biomass comprising undigested manure,
        ii. anaerobic inoculum comprising anaerobic hydrogenotrophic methanogenic organisms
    b. feeding the bioreactor with a second composition having a pH below that of the first composition,
    c. injecting $H_2$ containing gas into the bioreactor,
    d. collecting digested manure thus produced.
36. The method of item 35, further comprising refining the digested manure to a commercial grade fertilizer.
37. Use of the digested manure of item 35 or 36 as a fertilizer.
38. A bioreactor comprising:
    a. a reactor vessel,
    b. a gas injection system comprising hollow fibres
    c. loading means for supply of starting material, and
    d. discharge means for products and/or by-products.
39. The bioreactor of item 38, wherein the starting material is anaerobic inoculum comprising hydrogenotrophic methanogenic organisms, nutrients, acidic waste and/or biomass such as manure.
40. The bioreactor of item 39 wherein the gas injection system is used for supplying $H_2$ containing gas and/or raw low $CH_4$ content biogas to the reactor vessel.
41. The bioreactor of item 39, wherein the acidic waste is as defined in item 22.
42. The bioreactor of item 38 wherein the product is upgraded high $CH_4$ content biogas.
43. The method, the use or the bioreactor of any of the preceding items wherein the hydrogenotrophic methanogenic organisms is hydrogenotrophic methanogenic archaea.
44. The method, the use or the bioreactor of item 43 wherein the archaea comprises one or more species selected from the group consisting of *Methanobacterium alcaliphilum, Methanobacterium bryantii, Methanobacterium congolense, Methanobacterium defluvii, Methanobacterium espanolae, Methanobacterium formicicum, Methanobacterium ivanovii, Methanobacterium palustre, Methanobacterium thermaggregans, Methanobacterium uliginosum, Methanobrevibacter acididurans, Methanobrevibacter arboriphilicus, Methanobrevibacter gottschalkii, Methanobrevibacter olleyae, Methanobrevibacter ruminantium, Methanobrevibacter Methanobrevibacter woesei, Methanobrevibacter wolinii, Methanothermobacter marburgensis, Methanothermobacter thermautotrophicum, Methanothermobacter thermoflexus, Methanothermobacter thermophilus, Methanothermobacter wolfeii, Methanothermus sociabilis, Methanocorpusculum bavaricum, Methanocorpusculum parvum, Methanoculleus chikuoensis, Methanoculleus submarinus, Methanogenium frigidum, Methanogenium liminatans, Methanogenium marinum, Methanosarcina acetivorans, Methanosarcina barkeri, Methanosarcina mazei, Methanosarcina thermophila, Methanomicrobium mobile, Methanocaldococcus jannaschii, Methanococcus aeolicus, Methanococcus maripaludis, Methanococcus vannielii, Methanococcus voltaei, Methanothermococcus thermolithotrophicus, Methanopyrus kandleri, Methanothermobacter thermoautotroiphicus, Methanoca/dococcus fervens, Methanoca/dococcus indicus, Methanoca/dococcus infernus,* and *Methanoca/dococcus vulcanius.*
45. The method, the use or the bioreactor of any of the preceding items wherein the hydrogenotrophic methanogenic organism is a substantially pure culture of one hydrogenotrophic methanogenic archaea species.
46. The method, the use or the bioreactor of any of the preceding items wherein the conditions include a temperature of 35° C. to 37° C.
47. The method, the use or the bioreactor of the preceding items wherein the hydrogenotrophic methanogenic archea is Methanothermobacter thermoautotroiphicus.
48. The method, the use or the bioreactor of the preceding items wherein the conditions include a temperature of 50° C. to 60° C.

49. The method, the use or the bioreactor of the preceding items wherein the hydrogenotrophic methanogenic archea is selected from the group consisting of *Methanocaldococcus fervens*, *Methanocaldococcus indicus*, *Methanocaldococcus infernus*, and *Methanocaldococcus vulcanius*.

50. The method, the use or the bioreactor of the preceding items wherein the conditions include a temperature of 80° C. to 100° C.

51. The method, the use or the bioreactor of any of the preceding items wherein the anaerobic hydrogenotrophic methanogenic organism is contained in anaerobic sludge.

EXAMPLES

Example 1

In Situ Upgrading

Material and Methods
Substrate Characteristics

Substrates used in the experiment were cattle manure from Vegger biogas plant and whey from Vestforsyning A/S, Denmark. The substrates were received in one batch, mixed thoroughly and distributed in 5 L plastic bottles. It was kept at −20° C. for the whole period of experiment. The frozen substrates were thawed and kept at 4° C. for 2-3 days before use. Substrate characteristics were analyzed as illustrated in Table 2. Considering the high organic concentration of whey, it was diluted four times and then mixed with manure at a ratio 2:3.

TABLE 2-continued

| | Substrate characteristics | | |
|---|---|---|---|
| Parameters | Cattle manure | Whey | Mixture |
| $NH_4^+$—N (mg/L) | 540 ± 56 | 89 ± 25 | 330 ± 59 |

Reactor Setup and Operations

Two identical 1 L continuously stirred tank reactors (CSTR) (A and B) with working volume of 600 mL were used. Both reactors were filled with inoculum, which was digested manure from Snertinge biogas plant, in Denmark, operating under thermophilic conditions (55° C.). Temperature in the reactors was controlled at 55° C. The HRT was controlled at 15 days. The reactors were fed two times per day. Hydrogen was continuously added to Reactor A, while reactor B was operated as control, without hydrogen injection. The $H_2$ injection flow rate in reactor A was initially set at 1.5 L/d, and then changed to 1.7 L/d after 20 d operation, which was around 4 times higher than $CO_2$ production rate in the control reactor (B), corresponding to the stoichiometric ratio of $H_2$:$CO_2$ for production of $CH_4$. The hydrogen gas was injected to the bottom of reactor A either by a column diffuser (pore diameters 0.5-1.0 mm) or ceramic diffuser (14-40 um). The reactors were mixed by magnetic stirrer, and two different stirring speeds 150 and 300 rpm were tested. Detailed operation parameters could be found in Table 3.

TABLE 3

| | Performances of the reactors | | | | | |
|---|---|---|---|---|---|---|
| | Phase I | | Phase II | | Phase III | |
| Reactor | A | B | A | B | A | B |
| Mixing speed (rpm) | 150 | 150 | 300 | 300 | 150 | 150 |
| Gas diffuser | N | / | N | / | C | / |
| Biogas prodution rate (mL/(L · d)) | 1429 ± 157 | 874 ± 67 | 1235 ± 147 | 895 ± 45 | 1180 ± 130 | 873 ± 55 |
| Biogas composition (%) | | | | | | |
| $CH_4$ | 53 ± 3 | 55 ± 3.5 | 68 ± 2.5 | 56 ± 2.8 | 75 ± 3.4 | 56.7 ± 1.5 |
| $CO_2$ | 13 ± 1.5 | 45 ± 3.1 | 8.8 ± 1.8 | 44 ± 2.9 | 6.6 ± 1.2 | 43.3 ± 1.6 |
| $H_2$ | 34 ± 3.2 | / | 23.2 ± 2.3 | / | 18.4 ± 2.6 | / |
| $CH_4$ production rate (mL/L · d) | 757 ± 43 | 480 ± 31 | 839 ± 31 | 501 ± 25 | 885 ± 37 | 494 ± 22 |
| $CO_2$ production rate (mL/L · d) | 185 ± 36 | 393 ± 27 | 108 ± 35 | 393 ± 26 | 78 ± 24 | 378 ± 18 |
| $H_2$ consumption rate (mL/L · d) | 1185 ± 145 | / | 1384 ± 128 | / | 1452 ± 159 | / |
| pH | 7.74 ± 0.14 | 7.28 ± 0.12 | 7.84 ± 0.1 | 7.33 ± 0.07 | 7.89 ± 0.12 | 7.31 ± 0.13 |
| Acetate (mM) | 2.1 ± 0.1 | 0.6 ± 0.2 | 2.3 ± 0.2 | 0.5 ± 0.3 | 2.5 ± 0.4 | 0.8 ± 0.3 |
| Propionate (mM) | 0.8 ± 0.3 | 0.3 ± 0.1 | 0.7 ± 0.4 | 0.2 ± 0.1 | 0.5 ± 0.5 | 0.2 ± 0.1 |
| Effluent VS (g/L) | 8.9 ± 0.5 | 8.5 ± 0.6 | 7.8 ± 0.7 | 8.3 ± 0.4 | 8.4 ± 0.5 | 8.2 ± 0.8 |

TABLE 2

| | Substrate characteristics | | |
|---|---|---|---|
| Parameters | Cattle manure | Whey | Mixture |
| pH | 7.15 ± 0.11 | 4.33 ± 0.13 | 6.85 ± 0.10 |
| TS (g/L) | 30 ± 1.1 | 105 ± 2.1 | 28.5 ± 1.1 |
| VS (g/L) | 24.1 ± 1.2 | 98 ± 2.8 | 25 ± 1.4 |
| COD (g/L) | 40.4 ± 2.3 | 150 ± 5.7 | 40 ± 2.3 |
| TKN (mg/L) | 1092 ± 210 | 460 ± 78 | 701 ± 68 |

Pulse Load Tests

After the reactors had reached steady state, organic load pulses were introduced to compare the stability of anaerobic reactor with and without hydrogen addition. The tests were performed by feeding both reactors A and B with whey alone without dilution for two days. After that, the reactors were fed with the mixture again.

Results and Discussion

The performances of both reactors A and B at steady-states were summarized as shown in Table 3. The experiments were carried out for around 150 days. Steady state of each operation condition was obtained after around 2-3 HRT operation when VFA and biogas production had reached relatively stable values.

In the whole operation period, pH in reactor A was around 7.7-7.9, which was higher than that from reactor B (around 7.3). It was consistent with our previous study that addition of hydrogen to the anaerobic reactor would increase the pH. However, pH were always below 8 when co-digested manure with whey, which was suitable for methane production. The results supported our hypothesis that co-digestion of manure and whey could decrease the pH compared with manure alone (pH around 8.3).

During Phase I, $CH_4$ content in reactor A was only 53%, which was slightly lower than that from reactor B. However, the $CO_2$ content (13%) was much lower than that (45%) from reactor B. The $CH_4$ production rate of reactor A was around 58% higher compared with reactor B due to the conversion of $H_2$ and $CO_2$ to $CH_4$. In order to increase the hydrogen consumption rate and decrease the $H_2$ content in the biogas, the stirring speed was increased from 150 rpm to 300 rpm (Phase II). The $H_2$ consumption rate increased from 1185 to 1384 mL/L·d, which resulted in the increase of $CH_4$ content of reactor A to 68% and the decrease of $H_2$ content to 23%. It is obvious the increase of mixing was beneficial for high $CH_4$ content, which could be mainly due to the lower gas-liquid mass transfer limitations. However, the increase of mixing did not result in significant increase of $CH_4$ production rate of reactor B. The reason could be that 150 rpm was adequate to achieve homogeneous distribution of substrate, enzymes and microorganisms throughout the reactors. Previous studies also showed that vigorous mixing may disrupt the structure of microbial flocks and disturbs the syntrophic relationships between organisms thereby adversely affecting the reactor performances. In addition, the increase of mixing may significantly increase the operation cost, though it could help to increase the hydrogen consumption rate. Therefore, during Phase III, we decreased the stirring speed back to 150 rpm. Instead of intense mixing, we changed the $H_2$ distribution equipment from column diffuser to ceramic diffuser, which has smaller pores for better $H_2$ distribution. The $CH_4$ content further increased to 75%, which was much higher than that of reactor B. The above results indicated that high $CH_4$ content could be obtained by the increase of mixing or utilization of efficient $H_2$ distribution equipment. Utilization of efficient $H_2$ distribution equipment is recommended, because it is difficult to increase the mixing intensity in actual biogas plants. We calculated the theoretical $CH_4$ production rate based on the $H_2$ consumption rate and $CH_4$ production rate from reactor B at each operation condition, and the theoretical value was very close to the measured value, which indicated that the consumed hydrogen was almost fully converted to $CH_4$. Table 3 also showed that the addition of hydrogen did not influence the effluent VS concentration. Though there were small amount increase of acetate and propionate in reactor A compared with reactor B, their concentrations were still very low (<2 mM). It could be due to the optimal fermentation pH. The acetate concentration in our previous study were 24 mM and 7 mM in the anaerobic reactor fed with manure alone with and without $H_2$ addition, which could be due to the high pH (>8.0). It further demonstrated the superiority by co-digestion.

After Phase III, performances of reactors A and B under organic loading shock was tested by fed with whey alone without dilution for two days, and then the mixture was fed to the reactors again. For reactor A, the performance recovered within 5 days, and the pH was always higher than 7.0. However, the organic loading shock had significant effect on the performance of reactor B. There was large amount acetate accumulation, and it could be fully degraded only after around 10 day operation. Meanwhile, the accumulation of propionate was also observed, but it was still in a high level (8 mM) even after around 15 day operation. The pH in the reactor even decreased to lower than 6.5. The above results showed that the reactor with addition of $H_2$ was much stable and could bear the organic loading shock.

Example 2

Ex Situ Upgrading

Material and Methods

As sources of inoculum, mesophilic anaerobically digested sewage sludge (Wastewater treatment plant, Lundtofte, Denmark) and thermophilic anaerobically digested manure (Biogas plant, Snertinge, Denmark) were used.

Reactor Setup and Operation

The first experiment was conducted to compare the biogas upgrading potentials by mesophilic and thermophilic enriched mixed cultures. Initially, mixtures (380 mL) of mesophilic or thermophilic sludge and basal anaerobic (BA) medium [Angelidaki et al. (2004) Rev Environ Sci Biotech 3: 117-129] with VSS concentration 5 g/L were added in 1140 mL serum bottles. The BA medium contained 10 mM PBS buffer. The bottles were then closed with butyl-rubber stoppers and aluminum crimps and flushed with pure $H_2$. After that, pure $CO_2$ (190 mL) were injected into the bottles to achieve the ratio of $H_2/CO_2$ 4:1. The bottles were incubated in shakers at 37° C. (bottles inoculated with mesophilic sludge) and 55° C. (bottles inoculated with thermophilic inoculum) with shaking speed 300 rpm. The mixtures (25 mL) were replaced with fresh BA medium every day and at the same time the gases were also refreshed. The experiment lasted around 2 months. All the bottles were performed in duplicates. To determine the kinetics of $H_2$ consumption, enriched mesophilic and thermophilic cultures were incubated with different concentrations of $H_2$ in the headspace gas as described.

After one month operation of the first experiment, the second experiment was started under thermophilic condition with continuous feeding of gas. The reactor was 1 L bottle with 600 mL working volume. The reactor was filled with thermophilic inoculum and BA medium. The initial VSS concentration was 5 g/L. The feeding gas was composed of $H_2$, $CH_4$, $CO_2$ with the ratio 60:25:15. The gas was injected to the bottom of the reactor through ceramic gas diffusers. The initial gas flow rate was 3 L/(L·d) and then increased gradually. 40 mL mixture in the reactor was replaced with fresh BA medium everyday. The reactor was magnetically stirred at 500 or 800 rpm. Steady-state was defined with the differences of biogas production rate and component less than 10% in the consecutive six days.

Specific Methanogenic Activity (SMA) Tests

Acetoclastic and hydrogenotrophic methanogenic activities of the anaerobic cultures from both mesophilic and thermophilic reactors at the beginning and end of the enrichment were tested. 20 mL fresh samples were added in 68 mL bottles. Acetate (20 mM) or $H_2/CO_2$ (80/20, 1 atm) were supplemented to each bottle. Bottles with fresh samples only, but without substrates, were used as controls. The bottles were incubated in shakers at 37° C. or 55° C. with shaking speed 300 rpm. All the tests were prepared in duplicates.

Results and Discussion
Biogas Upgrading Potentials

Mesophilic and thermophilic mixed cultures were enriched to characterize their biomethanation potentials from $H_2$ and $CO_2$. The steady-states were achieved after one month cultivation. The long-term enrichments significantly increased the $H_2$ and $CO_2$ consumption rates under both mesophilic and thermophilic conditions. At the beginning of the enrichments, there were still $CO_2$ left even $H_2$ was fully consumed which could be due to the bicarbonate in the inoculum, which could react with $H_2$ and therefore decreased the $CO_2$ consumption in the gas phase. The $CO_2$ and $H_2$ could be almost fully consumed after long-term cultivation. At the end of the enrichment, it took around 4 h to achieve complete conversion of $H_2$ and $CO_2$ to $CH_4$ under thermophilic condition, while it took around 8 h under mesophilic condition.

Initially, both mesophilic and thermophilic cultures had acetoclastic and hydrogenotrophic methanogenic activities (around 10 mL $CH_4$/(gVSS·h)). However, the acetoclastic methanogenic activities could not be detected after long-term cultivation, while the hydrogenotrophic methanogenic activities increased to 198 mL $CH_4$/(gVSS·h) under mesophilic condition and 320 mL $CH_4$/(gVSS·h) under thermophilic condition.

The results indicated that hydrogenotrophic methanogens were selectively enriched, and thermophilic conditions should provide high efficiency for biogas upgrading.

Though acetate was found in both mesophilic (0.5 mM) and thermophilic (6.6 mM) enriched cultures, it was only equal to 0.14% and 1.9% of the produced $CH_4$. The acetate could be produced from homoacetogens [Luo et al. (2011) Biotech Bioeng 108: 1816-1827], and it needs to be further used by acetoclastic methanogens. Normally, in anaerobic digestion process, homoacetogens can not compete with hydrogenotrophic methanogens, due to their unfavorable thermodynamic characteristics [Siriwongrungson et al. (2007) Water Res 41: 4204-4210].

Biogas Upgrading Performance of Thermophilic Anaerobic Reactor

The biogas upgrading potentials were then tested in thermophilic continuously stirred tank reactor (CSTR), since the conversion of $H_2$ and $CO_2$ into $CH_4$ was significantly faster under thermophilic conditions compared to mesophilic operation. The operation parameters and results are shown in Table 4.

The inoculum has hydrogenotrophic methanogenic activity, and therefore more than half of the $H_2$ in the feeding gas was immediately consumed once start-up of the reactor. At day 10, the $CH_4$ content could be increased from 25% in the feeding gas to around 93% in the upgraded gas. After that, the gas loading rate increased to 6 L/(L·d) and the reactor was operated under this condition until steady-state was achieved. The $CH_4$ content could be as high as 95.4%, and there were only small amounts of $H_2$ and $CO_2$ left. The quality of the upgraded biogas was good enough to be used as natural gas. At day 44, the gas loading rate was further increased to 12 L/(L·d). However, the $CH_4$ content in the upgraded gas decreased to around 90% even after around one month operation. The gas-liquid mass transfer has been found as the limiting factor for bioconversion of gaseous substrate, especially when the gas (CO, $H_2$) has low solubility. Therefore, the mixing speed was increased from 500 rpm to 800 rpm at day 74 to lower the gas-liquid mass transfer limitations. The increase of mixing speed resulted in the increase of $CH_4$ content to around 95%. But there was no significant difference of the $H_2$ consumption rate between Phase II and III. It seems that intensive mixing of the liquid could reduce the $H_2$ content in the biogas, and thereby result in higher $CH_4$ content even under high gas loading rate. This point will be discussed later. After day 97, the gas loading rate increased to 24 L/(L·d). Though the decrease of $CH_4$ content was observed again, it is still around 90%. The above results showed that biogas upgrading could be achieved in thermophilic anaerobic reactor with high gas loading rate.

Theoretically, the ratio of $CH_4$ production rate to $H_2$ consumption rate should be 0.25. However, the value was more than 0.31 in the initial first 10 days. It could be explained by the excess $CH_4$ production from inoculum. After long-term operation, the effect of the inoculum was eliminated. The ratios were close to 0.25 during the steady-states of phase I, II, III and IV, which showed that the consumed $H_2$ was almost stoichiometrically converted to $CH_4$. Acetate was also detected as the main metabolite in the liquid phase with the concentration between 5.9-10.5 mM. Acetate as a metabolite in the mixed culture has been demonstrated in the first experiment. During the experiment, pH was relatively stable (around 7.8), which was favorable for methanogens.

TABLE 4

Performances of the thermophilic reactor under different operation conditions

| Period (day) | 0-10 | 11-43 (I) | 44-73 (II) | 74-96 (III) | 97-135 (IV) |
|---|---|---|---|---|---|
| Gas loading rate ($L/(L_{reactor} \cdot d)$) | 3 | 6 | 12 | 12 | 24 |
| Gas retention time (h) | 8 | 4 | 2 | 2 | 1 |
| Mixing speed (rpm) | 500 | 500 | 500 | 800 | 800 |
| Biogas production rate ($L/(L_{reactor} \cdot d)$) | 1.4 ± 0.3 | 2.5 ± 0.4 | 5.1 ± 0.6 | 4.9 ± 0.5 | 10.1 ± 1.3 |
| Biogas composition | | | | | |
| $CH_4$ (%) | 93.5 ± 4.4 | 95.4 ± 2.8 | 89.9 ± 4.1 | 94.2 ± 2.8 | 90.8 ± 2.4 |
| $CO_2$ (%) | 4.2 ± 2.5 | 0.7 ± 0.4 | 2.6 ± 1.5 | 1.9 ± 0.5 | 2.2 ± 1.3 |
| $H_2$ (%) | 2.3 ± 2.4 | 3.9 ± 0.8 | 7.5 ± 1.2 | 3.9 ± 0.7 | 7 ± 1.8 |
| $H_2$ consumption rate ($L/(L_{liquid} \cdot d)$) | 2.9 ± 0.5 | 5.9 ± 0.4 | 11.3 ± 0.7 | 11.6 ± 0.8 | 22.8 ± 2.1 |
| $CH_4$ production rate ($L/(L_{liquid} \cdot d)$) | 0.9 ± 0.2 | 1.5 ± 0.3 | 2.6 ± 0.5 | 2.7 ± 0.6 | 5.3 ± 1.4 |
| Yield $CH_4/H_2$ | 0.31 | 0.26 | 0.23 | 0.23 | 0.23 |
| Acetate concentration (mM) | 5.9 ± 1.2 | 8.8 ± 0.7 | 9.8 ± 1.3 | 10.5 ± 1.1 | 9.4 ± 1.6 |

Biogas upgrading by anaerobic digestion has not been studied before, and the results from this study showed that $CH_4$ content in the biogas around 90% or even higher could be achieved under thermophilic condition with gas loading rate up to 24 L/(L·d). In Denmark, there are more than 20 centralized biogas plants and cattle manure is the main substrate. The average production of biogas is 140 m³ per 100 m³ reactor tank. If the biogas upgrading concept proposed in the present study is applied in these biogas plants, an anaerobic reactor for biogas upgrading with volume 1/10 of the biogas reactor is needed. If more efficient gas-liquid mass transfer method is adopted, it is expected that even smaller reactor for biogas upgrading can be used. The economic and environmental analysis should be conducted in the future to make comparisons with the current technologies for biogas upgrading.

Example 3

Bioreactor Comprising Hollow Fibre Membrane (HFM)

Material and Methods
Experimental Setup

Figure 10:
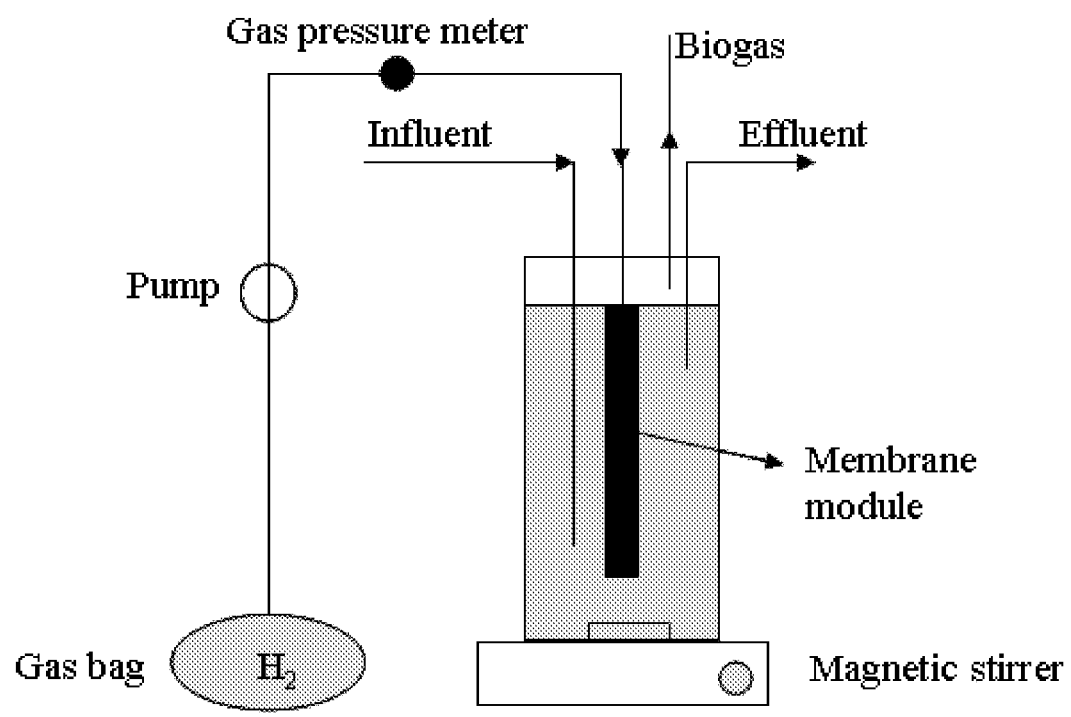
FIG. 10: Configuration of reactor A of Example 3.

Two identical 1 L continuously stirred tank reactors (CSTR) (A and B) with a working volume of 600 mL were used. Before the HFM was installed to reactor A, both reactors were fed with a mixture of cattle manure and whey (TS 28.5 g/L, VS 25 g/L, pH 6.85, detailed information is shown in Table 5) under thermophilic condition (55° C.) with 15 d hydraulic retention time (HRT). The purpose of using co-substrate is to maintain a suitable pH for anaerobic digestion. The reactors were mixed by magnetic stirrer at a stirring speed of 150 rpm and fed once per day. Similar performance was observed in the two reactors after around 1.5 months, and then a HFM module was installed in reactor A. The HFM module contained a bundle of 400 hollow fibre membranes (model MHF 200TL, Mitsubishi Rayon). For the HFM, nonporous thin polyurethane membrane is sandwiched between two porous polyethylene layers. The outside diameter and length of the fibre were 284 μm and 20 cm, respectively, providing a total surface area of 713 cm² for 400 HFM. $H_2$ was pumped to the HFM module from a gas bag using gas-tight tube. The daily $H_2$ flow rate was calculated by measuring the initial and residual $H_2$ inside the gas bag using 100 mL gas-tight syringe. Different $H_2$ flow rates were obtained by adjusting the speed (2, 3, 4 rpm) of peristaltic pump. The pressure inside the HFM module was monitored by a gas pressure meter. The configuration of reactor A is shown in FIG. 10.

Determination of $H_2$ Consumption Rate by the Biofilm Formed on the Membrane

During steady-state of each operation period, a similar reactor (C) as reactor A was used to test the $H_2$ consumption rate by the biofilm formed on the membrane. Reactor C was filled with BA medium (600 mL). $NaHCO_3$ (5 g/L) was added to the BA medium to provide $CO_2$ for $CH_4$ production. Reactor C was then flushed with a gas mixture of ($N_2/CO_2$, 80/20) and pre-incubated at 55° C. The pH was adjusted to 7.5 by adding 1N NaOH or 1N HCl. The HFM module was taken out from reactor A, and immediately inserted into reactor C. The reactor was mixed by magnetic stirrer at stirring speeds 150 rpm. A $H_2$ container was then connected with the HFM module, and the pressure inside the HFM module was controlled at the same level as that in reactor A. Since the bicarbonate in the liquid was consumed due to $H_2$ addition, increase of pH was expected. Therefore, the experiment only lasted for 4 hours to make sure that the pH inside the reactor was not significantly increased. The produced $CH_4$ was measured and was used for the calculation of $H_2$ consumption rate. The experiment was conducted twice at different periods with the same operation conditions, for statistical verification.

Specific Methanogenic Activity (SMA) Tests

Specific methanogenic activity assays on specific substrates during steady-state conditions of both reactors were carried out. 5 mL samples were immediately transferred from the reactors to 20 mL serum bottles. The samples were supplemented with either acetate (20 mM) or $H_2/CO_2$ (80/20, 1 atm) as substrates. Bottles with reactor samples only, but without substrates, were used as controls. The bottles were incubated in a shaker at 55° C. with shaking speed 300 rpm. All the tests were prepared in duplicates.

Scanning Electron Microscopy Imaging (SEM)

The HFM was prepared for SEM imaging. The sample was first fixed by a sequential two-step chemical immersion for 1 h each, first in 2% glutaraldehyde and then in 1% osmium tetroxide, both at pH 7.2 in 0.1M $NaPO_4$. Samples were dehydrated by successively passaging through 25, 50, 75, 80, 90, 95, 100% ethanol, and then dried by using vacuum drying apparatus. Then the samples were mounted on stubs and sputter-coated with gold-palladium. SEM imaging was carried out with a Quanta Scanning Electron Microscope.

Analytical Methods

TS, VS, $NH_3$—N, TKN and COD were analyzed according to APHA. Total inorganic carbon (TIC) was determined by a TOC-5000 (Shimadzu, Kyoto, Japan). The concentrations of acetate, butyrate, propionate were determined by gas chromatograph (GC) (Hewlett Packard, HP5890 series II) equipped with a flame ionization detector and HP FFAP column (30 m×0.53 mm×1.0 μm). $H_2$ was analyzed by GC-TCD fitted with a 4.5 m×3 mm s-m stainless column packed with Molsieve SA (10/80). $CH_4$ was analyzed with GC-TCD fitted with paralleled column of 1.1 m×3/16 "Molsieve 137 and 0.7 m×1/4" chromosorb 108.

Calculation of Inorganic Carbonate Species ($CO_2$, $HCO_3$)

TIC consists of the three species soluble $CO_2$, $HCO_3^-$ and $CO_3^{2-}$. The fractional ionization factor for carbonic acid ($a_o$) was calculated using the following equations:

$$\alpha_0 = \frac{[CO_2]}{TIC} = \frac{[H^+]^2}{[H^+]^2 + [H^+]^2 \cdot K_{a,1} + K_{a,1} \cdot K_{a,2}} \quad (2)$$

$$K_{a,1} = \frac{[H^+][HCO_3^-]}{[CO_2]} \quad (3)$$

$$K_{a,2} = \frac{[H^+][CO_3^{2-}]}{[HCO_3^-]} \quad (4)$$

$$TIC = [CO_2] + [HCO_3^-] + [CO_3^{2-}] \quad (5)$$

The $K_a$ values ($K_{a,1}$ is $10^{-6.18}$, $K_{a,2}$ is $10^{-10.07}$, at 55° C.) was obtained by making temperature corrections to that at 25° C. by Van't Hoff relationship. Based on the above equations, the inorganic carbonate species were calculated.

Results and Discussion

Figure 5:
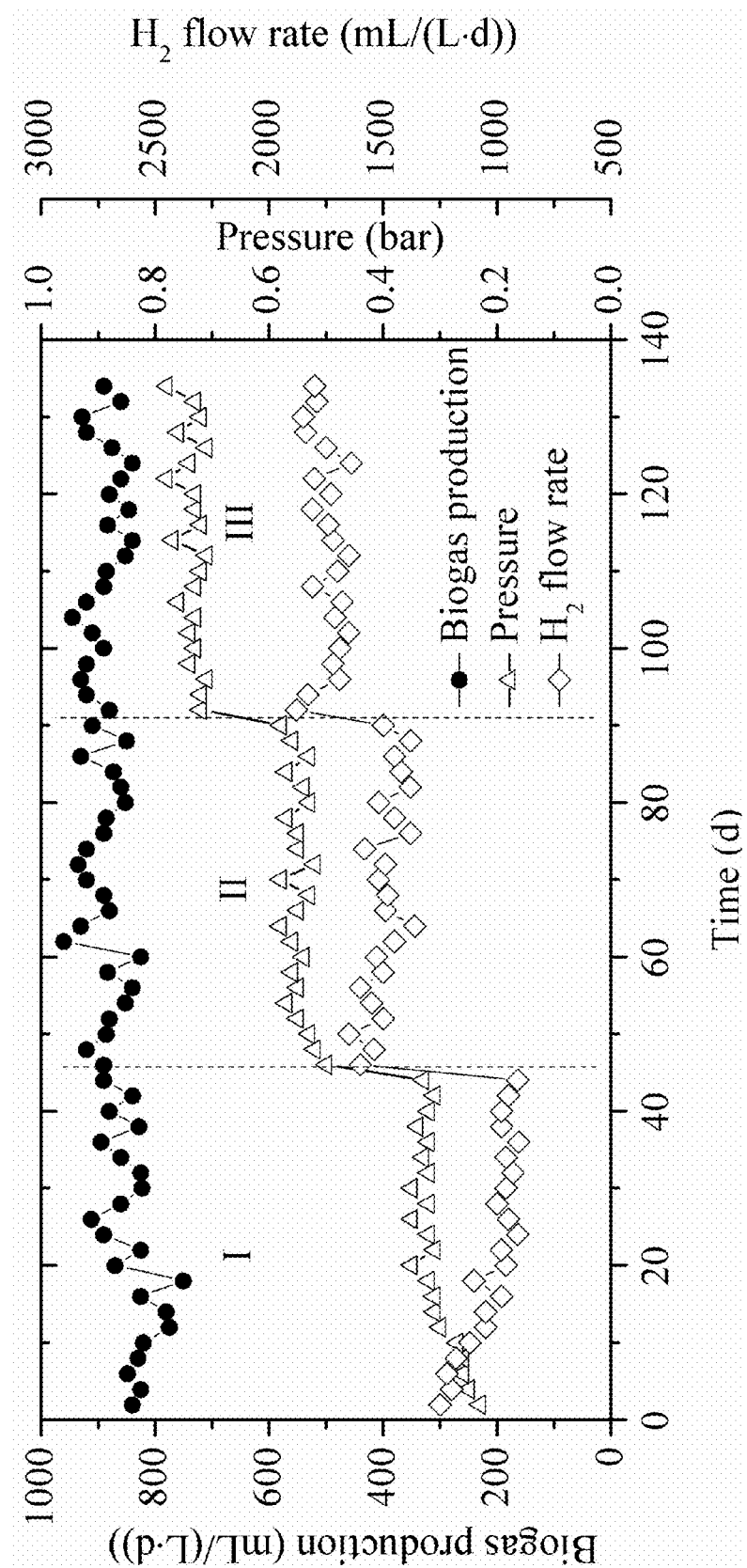
FIG. 5: Profiles of biogas production, pressure and $H_2$ flow rate of reactor A
Figure 6:
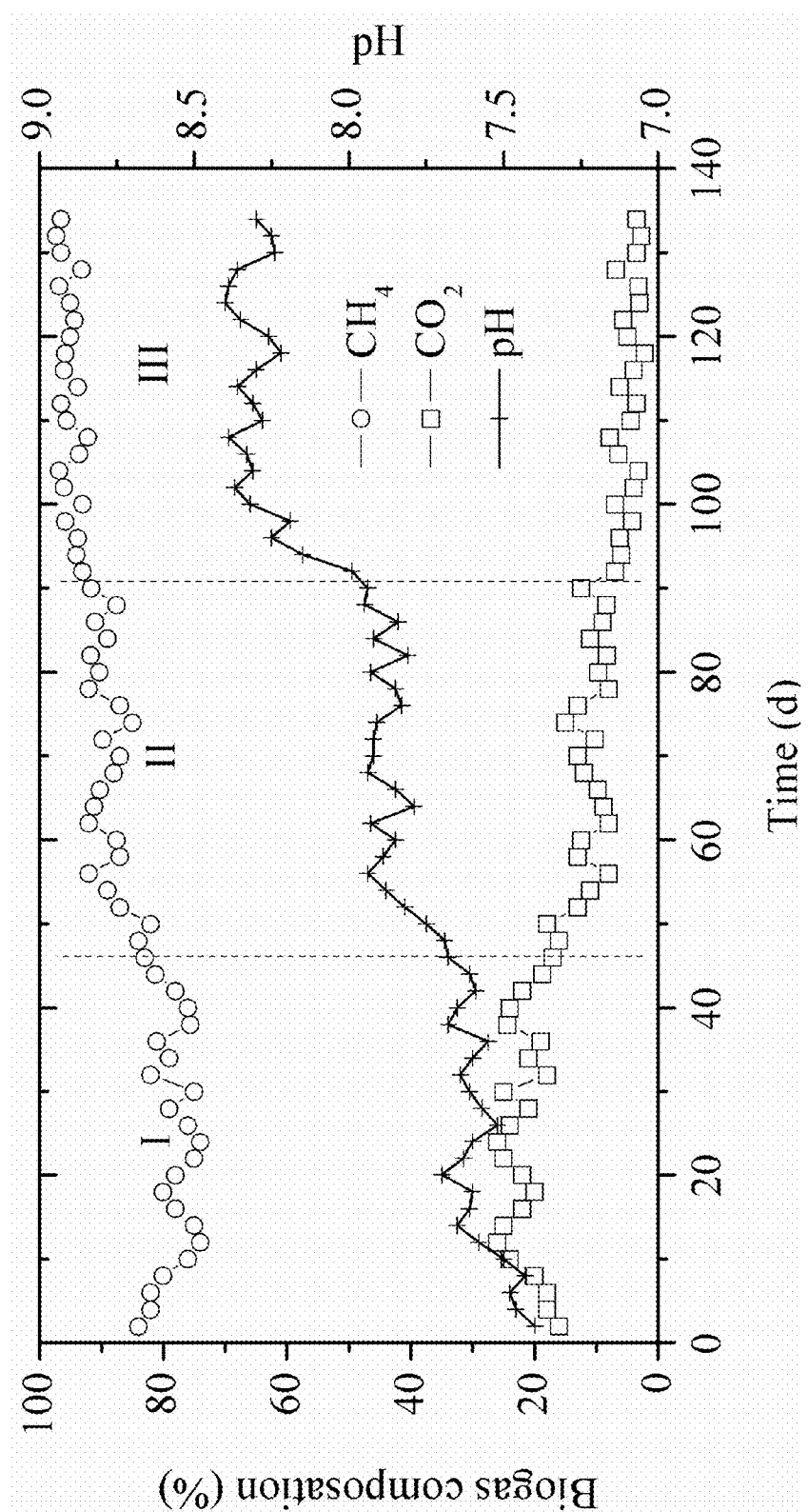
FIG. 6: Profiles of biogas composition and pH of reactor A

Data from operation of both reactors A and B during steady-states is summarized in Table 5. FIGS. 5 and 6 shows the time-courses of key parameters (biogas production, hydrogen flow rate, biogas composition etc) in reactor A throughout the study. Reactor B was stable during the whole operation period, and thus the time-course of the measured parameters are not shown. Steady state at each operation condition in reactor A was obtained after operation for approximately 2-3 HRTs, when VFA and biogas production had reached relatively stable values (max. 10% daily variation).

TABLE 5

Summary of steady-state reactor performances

| | Phase I (days 1-45) | | Phase II (days 46-91) | | Phase III (days 92-134) | |
|---|---|---|---|---|---|---|
| Reactor | A | B | A | B | A | B |
| Speed of the pump (rpm) | 2 | / | 3 | / | 4 | / |
| Gas pressure (bar) | 0.32 ± 0.01 | / | 0.56 ± 0.02 | / | 0.75 ± 0.03 | / |
| $H_2$ flow rate (mL/(L·d)) | 930 ± 50 | / | 1440 ± 80 | / | 1760 ± 100 | / |
| $H_2$ flow rate (mol $H_2/(m^2 \cdot d)$) | 0.35 | / | 0.54 | / | 0.66 | / |
| Biogas production rate (mL/(L·d)) | 868 ± 37 | 847 ± 24 | 885 ± 39 | 853 ± 36 | 895 ± 29 | 865 ± 25 |
| Biogas composition (%) | | | | | | |
| $CH_4$ | 78.4 ± 1.3 | 54.2 ± 1.6 | 90.2 ± 2.4 | 53.1 ± 1.5 | 96.1 ± 1.1 | 55.4 ± 1.8 |
| $CO_2$ | 21.6 ± 1.7 | 45.8 ± 1.3 | 9.8 ± 1.3 | 46.9 ± 1.6 | 3.9 ± 1.3 | 44.6 ± 1.9 |
| $CH_4$ yield (mL/gVS) | 268 ± 24 | 274 ± 16 | 262 ± 31 | 271 ± 19 | 251 ± 22 | 286 ± 17 |
| pH | 7.61 ± 0.06 | 7.29 ± 0.08 | 7.9 ± 0.1 | 7.28 ± 0.11 | 8.31 ± 0.12 | 7.3 ± 0.1 |
| Acetate (mM) | 3.5 ± 0.2 | 1.2 ± 0.3 | 10.2 ± 0.8 | 1.4 ± 0.5 | 36 ± 2.1 | 1.5 ± 0.3 |
| Propionate (mM) | 0.8 ± 0.2 | 0.4 ± 0.1 | 1.6 ± 0.2 | 0.3 ± 0.1 | 1.8 ± 0.4 | 0.4 ± 0.1 |
| Effluent VS (g/L) | 8.3 ± 0.4 | 8.4 ± 0.5 | 8.2 ± 0.5 | 8.4 ± 0.9 | 10.2 ± 0.5 | 8.5 ± 0.6 |
| Total inorganic carbon (mM) | 102 ± 8 | 115 ± 11 | 85 ± 5 | 120 ± 12 | 66 ± 7 | 110 ± 11 |

Figure 7:
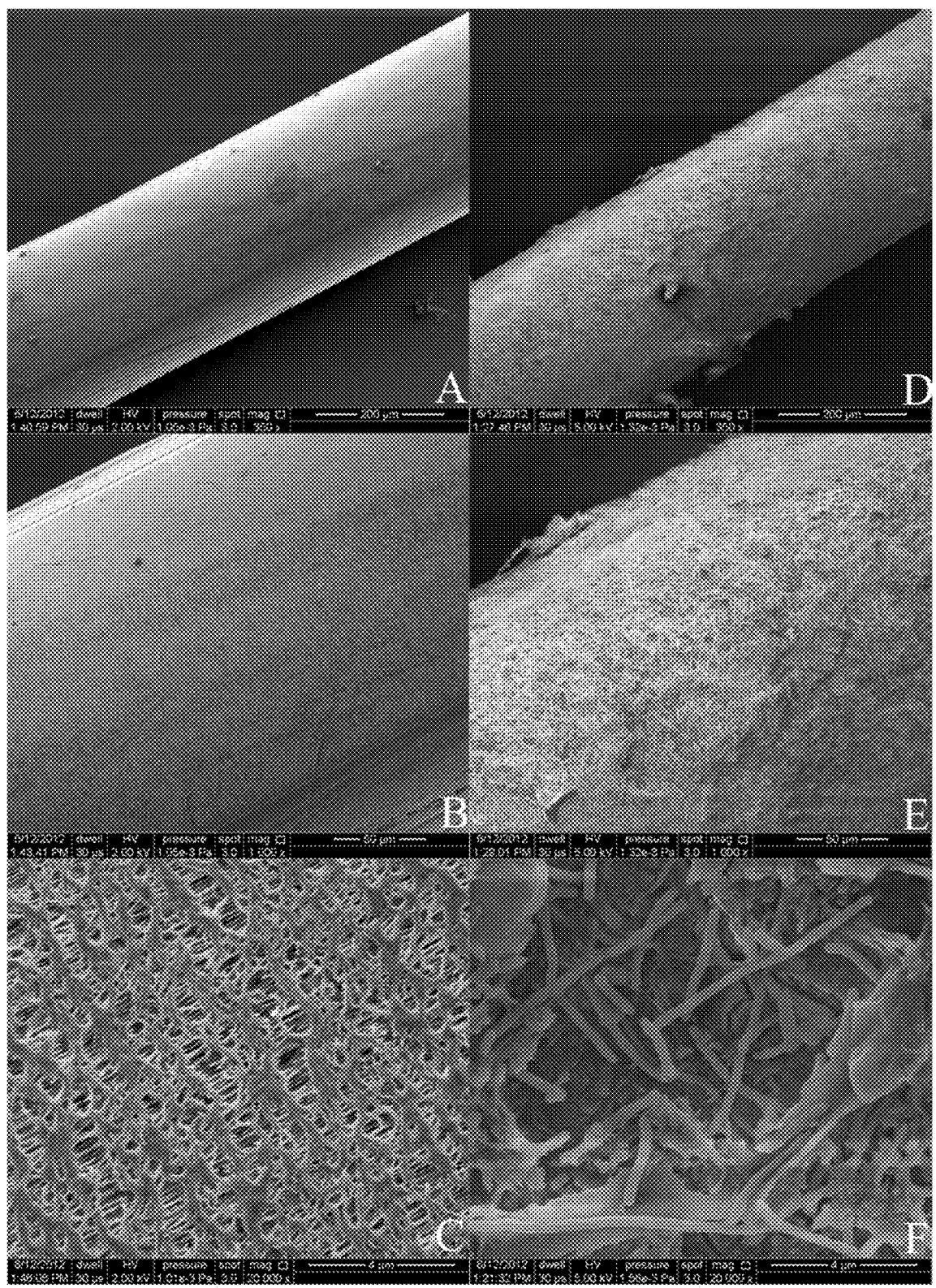
FIG. 7: Scanning Electron Microscopy (SEM) images of the Hollow Fiber Membrane (HFM): raw HFM (A-C), HFM in the reactor (D-F). Settings were as follows:
A—dwell: 30 ps, HV: 2.00 kV; pressure: $1.05e^{-3}$ Pa; Spot: 3.0; Mag: 350×
B—dwell: 30 ps, HV: 2.00 kV; pressure: $1.05e^{-3}$ Pa; Spot: 3.0; Mag: 1,000×
C—dwell: 30 ps, HV: 2.00 kV; pressure: $1.05e^{-3}$ Pa; Spot: 3.0; Mag: 20,000×
D—dwell: 30 ps, HV: 5.00 kV; pressure: $1.32e^{-3}$ Pa; Spot: 3.0; Mag: 350×
E—dwell: 30 ps, HV: 5.00 kV; pressure: $1.32e^{-3}$ Pa; Spot: 3.0; Mag: 1,000×
F—dwell: 30 ps, HV: 5.00 kV; pressure: $1.58e^{-3}$ Pa; Spot: 3.0; Mag: 20,000×

During the whole operational period, there was no detectable $H_2$ in the biogas of reactor A. In phase I, the $H_2$ pumping speed was set at 2 rpm. The $CH_4$ content in reactor A increased to around 82% once $H_2$ was fed to the reactor, which indicated that there was high hydrogenotrophic methanogenic activity in reactor A. Obvious increase of $H_2$ pressure from 0.23 bar to 0.32 bar inside the HFM module was observed during the first 20 days, and it resulted in decrease of $H_2$ flow rate to the reactor. The $H_2$ flow rate decreased from around 1200 mL/(L·d) to 930 Ml/(L·d). The increase of $H_2$ pressure may be attributed to biofilm formation on the surface of HFM, which increased the resistance of $H_2$ diffusion from inside of the hollow fibre to the liquid. A dark grey color, indicating formation of a biofilm, was observed on the surface of HFM. SEM results are shown in FIG. 7. The surface of the raw HFM is porous, however, the porous structure could not be observed on the surface of the HFM at the end of the operation. Biofilm formation is a common phenomenon, and it is very important in a membrane biofilm reactor to retain microorganism in the reactor. However, it seems that biofilm formation is undesirable in our study since there was already sufficient microbial activity in the liquid, while biofilm formation decreased the efficiency of the hydrogen supply.

After 20 days operation, the $H_2$ pressure was relatively stable at around 0.32 bar, which indicated that a stable biofilm structure was formed on the HFM. During the steady-state of phase I, the $H_2$ flow rate was 930 mL/(L·d), and the $CH_4$ content in the biogas was 78%. In order to further increase the $CH_4$ content, the $H_2$ pumping speed was adjusted to 3 rpm in phase II. Consequently, the $H_2$ pressure inside the HFM increased to 0.56 bar and the $H_2$ flow rate increased to 1440 mL/(L·d). The $CH_4$ content was increased to around 90% in phase II. Further increase of $H_2$ pumping speed to 4 rpm in phase III resulted in the even higher $CH_4$ content (96%) due to the higher $H_2$ flow rate (1760 mL/(L·d)). No further increase of the pumping speed was tested, as the pH in the anaerobic reactor rose to 8.3, which was the upper pH limit for microbial growth. The present study showed that high $CH_4$ content (>96%) was achieved for $H_2$ assisted in-situ biogas upgrading by HFM.

Besides the $CH_4$ content, the $CH_4$ yield is also a key parameter for evaluation of the in-situ biogas upgrading process under different operation conditions. Assuming the consumed $H_2$ was fully converted to $CH_4$, the $CH_4$ yield from the organic substrate could be calculated and the data is shown in Table 5. The differences between reactor A and B were lower than 5% in phase I and II. During phase I and II, the pH was always below 8.0. However, the $CH_4$ yield of reactor A was around 12% lower than that of reactor B in phase III. The lower $CH_4$ yield of reactor A was consistent with the higher effluent VS and acetate concentration. It suggested that the $CH_4$ production from the organic wastes was inhibited in phase III in reactor A. It was probably due to the high pH (8.31) in reactor A which inhibited methanogenic activity.

TABLE 6

Specific methanogenic activity on different substrates ($mLCH_4/gVS \cdot d$) in reactors A and B at steady-states

| | Phase I | | Phase II | | Phase III | |
|---|---|---|---|---|---|---|
| Reactor | A | B | A | B | A | B |
| Acetate | 123 ± 27 | 117 ± 21 | 116 ± 26 | 125 ± 18 | 90 ± 14 | 131 ± 29 |
| $H_2/CO_2$ | 295 ± 25 | 210 ± 18 | 330 ± 23 | 201 ± 29 | 352 ± 28 | 221 ± 33 |

From Table 6, it can be seen that the activity of acetoclastic methanogens from reactor A (90 mLCH$_4$/(gVS·d)) was lower than that from reactor B (131 mLCH$_4$/(gVS·d)) in phase III. In the present study, co-substrate of manure and whey was used, and it seems that once we maintained the pH below 8.0 by controlling the H$_2$ flow rate using HFM, maximum CH$_4$ content of 90% was achieved without inhibition of the original anaerobic process. If higher CH$_4$ content is required, it is necessary to increase H$_2$ flow rate and at the same time control the pH below 8.0 by on-line pH control. In the present study, there was no obvious accumulation of propionate during all the three phases in reactor A, which showed that injection of H$_2$ by HFM did not inhibit the propionate degradation. It was mainly due to the fast consumption of H$_2$ by the microorganisms in the reactor, which resulted in the low soluble H$_2$ concentration and made the degradation of propionate thermodynamically feasible.

Figure 8:
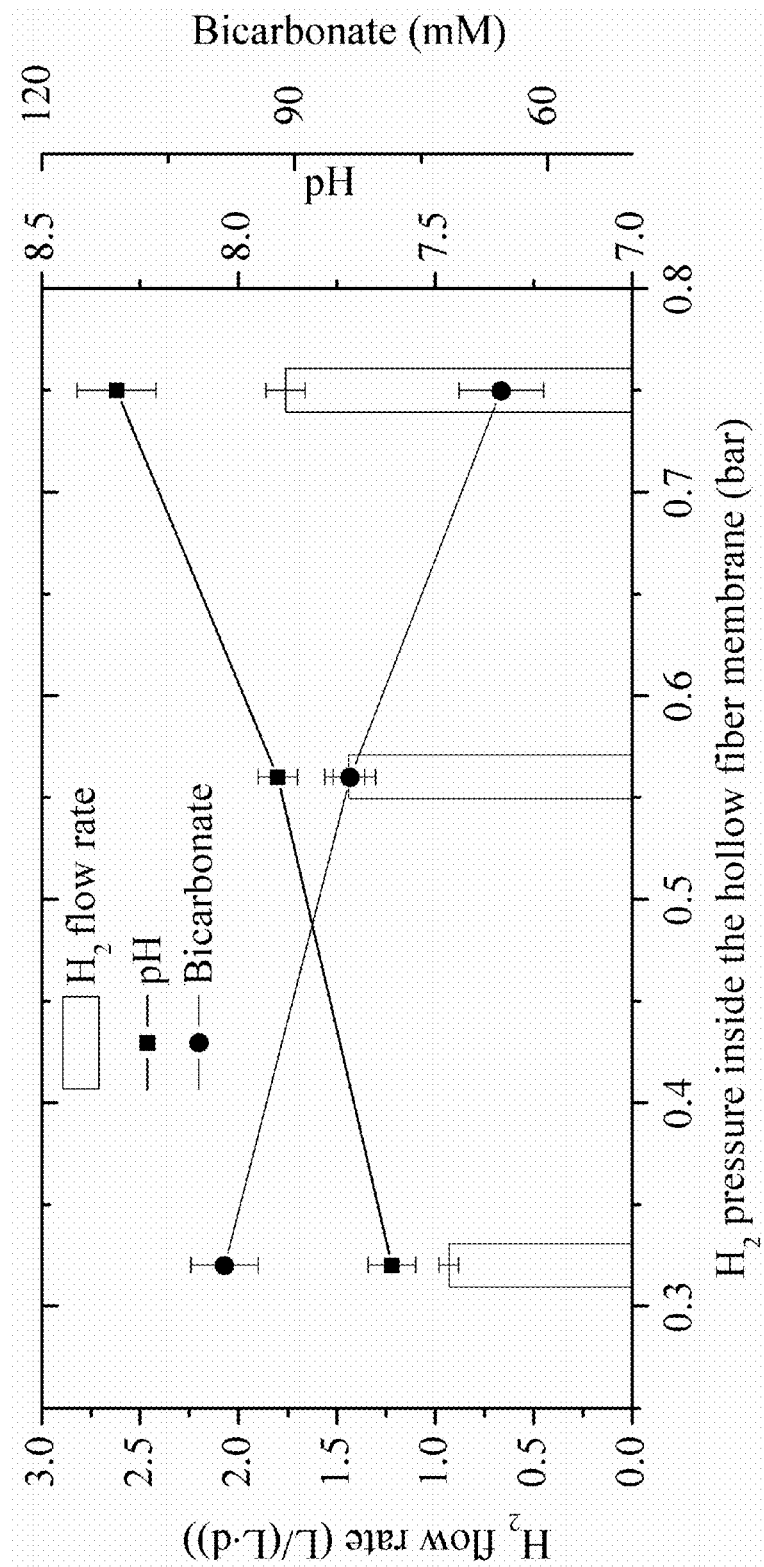
FIG. 8: $H_2$ flow rate, pH and bicarbonate in reactor A according to $H_2$ pressure inside the HFM in each steady state.
Figure 9:
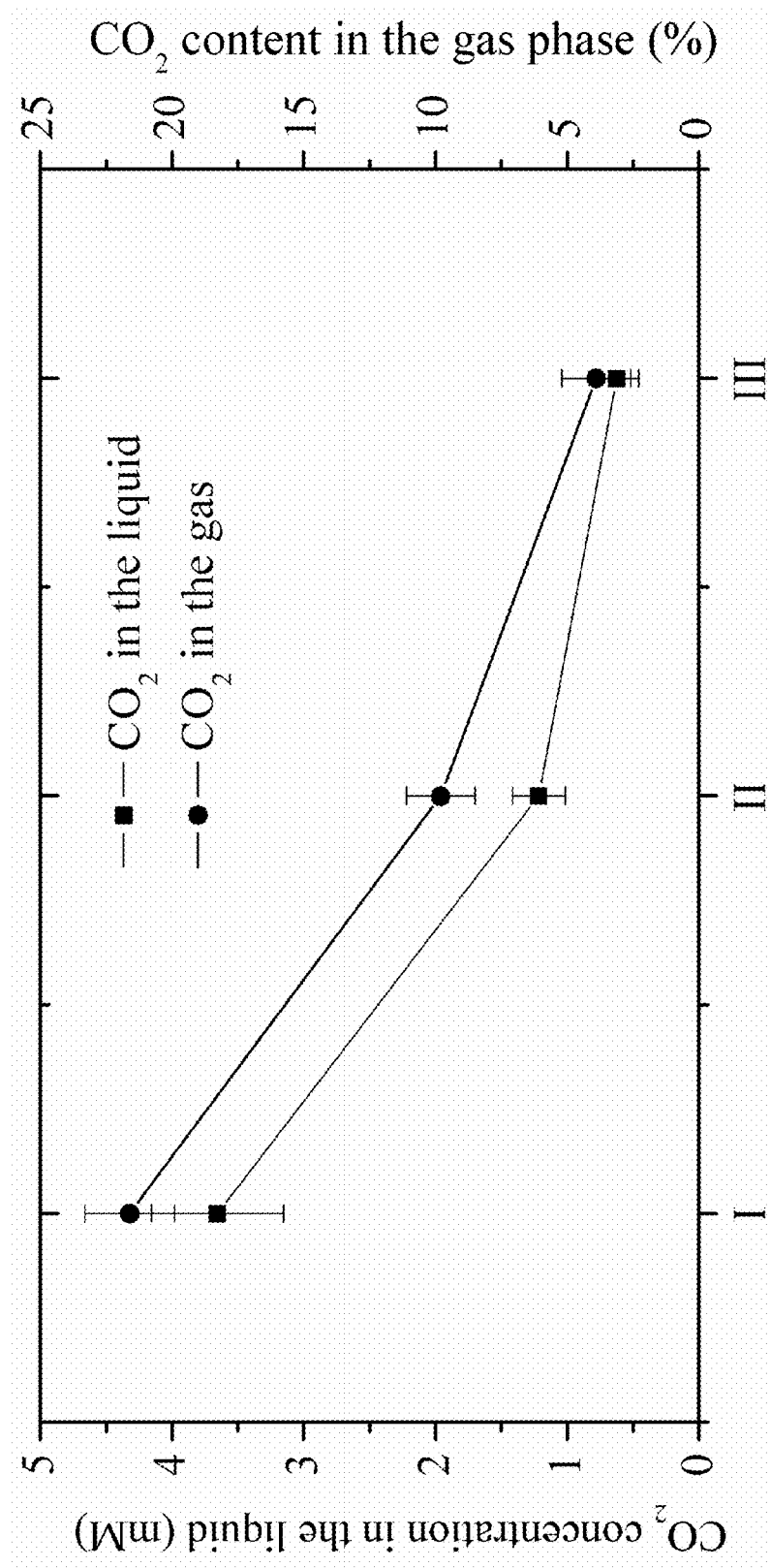
FIG. 9: $CO_2$ in the liquid and gas phase in reactor A in each steady state.

FIG. 8 shows the H$_2$ pressure, H$_2$ flow rate, pH and bicarbonate during steady state of each operational period. It is obvious that increase of H$_2$ pressure was coinciding with increase of H$_2$ flow rate and pH. Based on the inorganic carbon concentration, the soluble CO$_2$ was calculated and it was shown in FIG. 9. The CO$_2$ content in the biogas was also plotted in FIG. 9. The decrease of soluble CO$_2$ from phase I to III was consistent with the decrease of CO$_2$ content in the biogas. Generally, CO$_2$ can be assumed to be in thermodynamic equilibrium between liquid and gas phase considering its high solubility. Therefore, Henry's law is used to describe the relationship between soluble and liquid CO$_2$.

$$p = k_{H,pc} * x \quad (6)$$

Where P is the partial pressure of CO$_2$, $k_{H,pc}$ is the Henry's law constant, 1.63 L·atm/mol, x is the soluble CO$_2$ concentration, mol/L. From equation 6, the CO$_2$ content in gas phase is proportional to the soluble CO$_2$ in the liquid, which is consistent with our results. The soluble CO$_2$ is related to both pH and TIC (equation 2), and the lower concentration of soluble CO$_2$ can be obtained by either increasing the pH or decreasing the inorganic carbon concentration. In our study, both increase of pH and decrease of inorganic carbon concentration were observed, which finally led to lower CO$_2$ concentration.

The total H$_2$ consumption rate and the H$_2$ consumption rate by the biofilm on the surface of HFM at each operational condition were calculated and listed in Table 7.

TABLE 7

Total H$_2$ consumption rate and H$_2$ consumption rate by the biofilm of reactor A

| | Phase I | Phase II | Phase III |
|---|---|---|---|
| Total H$_2$ consumption rate (mL/d) | 560 | 864 | 1056 |
| H$_2$ consumption rate by the biofilm (mL/d) | 200 | 224 | 232 |
| Ratio (%) | 36% | 26% | 22% |

The H$_2$ consumption rates by the biofilm were 200, 224 and 232 mL/d in phase I, II and III, respectively. However, the H$_2$ consumption rate by the biofilm only accounted for 36%, 26% and 22% of the total H$_2$ consumption rate in phase I, II and III, respectively. This indicated that most of the H$_2$ was consumed by the suspended sludge in the liquid, and it was further proven by the SMA results. In each phase, the SMA of the suspended sludge on H$_2$ from reactor A was always higher than that from the control reactor B. The above results showed that both the biofilm and suspended sludge were contributing to the H$_2$ consumption in our HFM based anaerobic reactors. The biofilm increased the resistance of H$_2$ transferred to the liquid, and as a consequence pumping speed and thereby the energy consumption should be increased, in order to maintain constant supply of H$_2$ to the reactor. The biofilm structure is ultimately a function of the interactive strength between aggregates and hydrodynamic shear force. A previous study of a membrane biofilm reactor for H$_2$-driven denitrification of municipal wastewater (Celmer et al. 2008. Water Research 42(12)) showed that different biofilm structures (thickness, density) were formed as a result of different mixing intensities. It is obvious that reducing the biofilm thickness by intensive mixing leads to higher gas permeation rate. However, increase of mixing intensity is not practical for anaerobic reactors, due to increase of the operation costs. Additionally, increase of mixing intensity has been proven not to be beneficial for the biogas production. A possible way to remove biofilm is to wash the HFM module periodically.

In our study we successfully applied HFM in an anaerobic reactor for H$_2$ assisted in-situ biogas upgrading, which solved the problem of low CH$_4$ content and high H$_2$ content in the produced biogas. A CH$_4$ content of 90-96% was achieved in the present study.

The invention claimed is:
1. A method of manufacturing an upgraded biogas in situ, said method comprising the steps of:
   a. initiating an anaerobic digestion process in a bioreactor comprising:
      i. substrate,
      ii. anaerobic inoculum comprising anaerobic hydrogenotrophic methanogenic organisms,
   b. feeding the bioreactor with an acidic waste substrate to lower the pH in the bioreactor, to maintain a pH between 7 and 8,
   c. feeding the bioreactor with biomass,
   d. injecting H$_2$ containing gas into the bioreactor, and
   e. collecting the upgraded biogas thus produced, wherein said upgraded biogas derived from the substrate, acidic waste substrate, and the biomass, has a CH$_4$ concentration of at least 90%.
2. The method of claim 1, wherein the substrate of step a) i. is biomass.
3. The method of claim 2, wherein the biomass is protein-rich organic waste selected from the group consisting of manure, activated sludge from a wastewater treatment plant and fish processing residues.
4. The method of claim 2, wherein the biomass is manure.
5. The method of claim 1, wherein the acidic waste is a carbohydrate-rich waste selected from the group consisting of whey, stillage, fruit juice, and waste from potato processing industries.
6. The method of claim 1, wherein the acidic waste is whey.
7. The method of claim 1, wherein the acidic waste and biomass is fed to the bioreactor once or several times a day.
8. The method of claim 1, wherein the ratio of biomass to acidic waste fed to the reactor is 3 to 2.
9. The method of claim 1, wherein the ratio of biomass to acidic waste is 1 to 1.
10. The method of claim 1, wherein the H$_2$ containing gas consists essentially of H$_2$.
11. The method of claim 1 further comprising the steps of:
   a. transferring the upgraded biogas produced in the bioreactor in step e) to a second bioreactor, wherein an anaerobic digestion process has been initiated with:

i. nutrients,
   ii. anaerobic inoculum comprising anaerobic hydrogenotrophic methanogenic organisms,
  b. feeding the second bioreactor with nutrients,
  c. injecting $H_2$ containing gas into the second bioreactor, and
  d. collecting the upgraded biogas thus produced, thereby producing a further upgraded biogas.

12. The method of claim 11, wherein the $H_2$ containing gas is co-injected into the second bioreactor together with the upgraded biogas produced in step e).

13. The method of claim 11, wherein the nutrients are micro and macro nutrients necessary for microbial growth.

14. The method of claim 11, wherein the $CH_4$ concentration of the further upgraded biogas produced in step d) is at least 95%.

15. The method of claim 1 further comprising a step of separating $CH_4$ from other components of the upgraded biogas produced, thus further increasing the concentration of $CH_4$.

16. The method of claim 1, wherein the bioreactor comprises a gas injection system comprising hollow fibres.

17. The method of claim 1, wherein the hydrogenotrophic methanogenic organisms is hydrogenotrophic methanogenic archaea.

18. The method of claim 17, wherein the archaea comprise one or more species selected from the group consisting of *Methanobacterium alcaliphilum, Methanobacterium bryantii, Methanobacterium congolense, Methanobacterium defluvii, Methanobacterium espanolae, Methanobacterium formicicum, Methanobacterium ivanovii, Methanobacterium palustre, Methanobacterium thermaggregans, Methanobacterium uliginosum, Methanobrevibacter acididurans, Methanobrevibacter arboriphilicus, Methanobrevibacter gottschalkii, Methanobrevibacter olleyae, Methanobrevibacter ruminantium, Methanobrevibacter smithii, Methanobrevibacter woesei, Methanobrevibacter wolinii, Methanothermobacter marburgensis, Methanothermobacter thermautotrophicum, Methanothermobacter thermoflexus, Methanothermobacter thermophilus, Methanothermobacter wolfeii, Methanothermus sociabilis, Methanocorpusculum bavaricum, Methanocorpusculum parvum, Methanoculleus chikuoensis, Methanoculleus submarinus, Methanogenium frigidum, Methanogenium liminatans, Methanogenium marinum, Methanosarcina acetivorans, Methanosarcina barkeri, Methanosarcina mazei, Methanosarcina thermophila, Methanomicrobium mobile, Methanocaldococcus jannaschii, Methanococcus aeolicus, Methanococcus maripaludis, Methanococcus vannielii, Methanococcus voltaei, Methanothermococcus thermolithotrophicus, Methanopyrus kandleri, Methanothermobacter thermoautotroiphicus, Methanocaldococcus fervens, Methanocaldococcus indicus, Methanocaldococcus infernus,* and *Methanocaldococcus vulcanius.*

19. The method of claim 1, wherein the hydrogenotrophic methanogenic organism is a pure culture of one hydrogenotrophic methanogenic archaea species.

20. A method of upgrading a biogas in situ, comprising:
  providing a bioreactor having anaerobic hydrogenotrophic methanogenic organisms and an initial substrate to form a biogas within the bioreactor;
  injecting hydrogen into the bioreactor, in a sufficient amount to reduce a carbon dioxide portion of the biogas within the bioreactor to methane and causing a corresponding increase in pH;
  feeding the bioreactor with a mixture of an amount of a biomass and an amount of an acidic waste substrate at least once per day, a ratio of the acidic waste substrate to the biomass being controlled to reduce the pH in the bioreactor to a pH between 7 and 8; and
  collecting the upgraded biogas derived from the substrate, acidic waste substrate, and the biomass, having a methane concentration of at least 90%.

\* \* \* \* \*